(12) United States Patent
Rabiner et al.

(10) Patent No.: US 9,775,661 B2
(45) Date of Patent: Oct. 3, 2017

(54) DEVICES AND METHODS FOR BONE RESTRUCTURE AND STABILIZATION

(75) Inventors: Robert A. Rabiner, Tiverton, RI (US); Richard Scott Rader, Wayland, MA (US)

(73) Assignee: IlluminOss Medical, Inc., East Providence, RI (US)

(*) Notice: Subject to any disclaimer, the term of this patent is extended or adjusted under 35 U.S.C. 154(b) by 18 days.

(21) Appl. No.: 13/553,247

(22) Filed: Jul. 19, 2012

(65) Prior Publication Data

US 2013/0023886 A1 Jan. 24, 2013

Related U.S. Application Data

(60) Provisional application No. 61/509,391, filed on Jul. 19, 2011, provisional application No. 61/509,314, (Continued)

(51) Int. Cl.
*A61B 17/88* (2006.01)
*A61B 17/74* (2006.01)
(Continued)

(52) U.S. Cl.
CPC ...... *A61B 17/8855* (2013.01); *A61B 17/7097* (2013.01); *A61B 17/72* (2013.01);
(Continued)

(58) Field of Classification Search
CPC ..... A61B 17/72; A61B 17/74; A61B 17/8855; A61B 17/8858; A61B 17/7097;
(Continued)

(56) References Cited

U.S. PATENT DOCUMENTS 3,485,520 A * 12/1969 Alexander ............... B23G 1/46
15/145
4,271,839 A * 6/1981 Fogarty et al. ............... 606/194
(Continued)

FOREIGN PATENT DOCUMENTS

DE 40 28 466 3/1992
EP 0 709 698 5/1996
(Continued)

OTHER PUBLICATIONS

USPTO Office Action in U.S. Appl. No. 13/772,947 mailed Jun. 19, 2013.
(Continued)

*Primary Examiner* — Matthew Lawson
*Assistant Examiner* — Amy Sipp
(74) *Attorney, Agent, or Firm* — Greenberg Traurig, LLP; David J. Dykeman; Roman Fayerberg

(57) ABSTRACT

Devices and methods for restructure and stabilization of a fractured or weakened head of a bone are disclosed herein. A device includes a delivery catheter having a proximal end and a distal end, an inner void for passing at least one light sensitive liquid, and an inner lumen; an expandable member releasably engaging the distal end of the delivery catheter; and a light conducting fiber sized to pass through the inner lumen of the delivery catheter and into the expandable member. The expandable member moves from a deflated state to an inflated state when the light sensitive liquid is passed to the expandable member. When the light conducting fiber is in the expandable member, the light conducting fiber is able to disperse the light energy to initiate hardening of the light sensitive liquid within the expandable member to form a photodynamic implant.

23 Claims, 11 Drawing Sheets

Related U.S. Application Data filed on Jul. 19, 2011, provisional application No. 61/509,459, filed on Jul. 19, 2011.

(51) Int. Cl.

| | | |
|---|---|---|
| *A61B 17/72* | (2006.01) | |
| *A61B 17/70* | (2006.01) | |
| *A61N 5/06* | (2006.01) | |

(52) U.S. Cl.
CPC .......... *A61B 17/7275* (2013.01); *A61B 17/74* (2013.01); *A61B 17/8836* (2013.01); *A61B 17/8858* (2013.01); *A61N 5/06* (2013.01); *A61N 5/062* (2013.01)

(58) Field of Classification Search
CPC ............ A61B 17/8833; A61B 17/8836; A61B 17/8852; A61B 17/885; A61B 17/8802–17/8847; A61B 2017/883; A61B 2017/8813–2017/8844; Y10T 403/7039; F16B 17/00
USPC ..... 606/62, 63, 326–327, 92–94, 64, 67, 68; 623/23.62
See application file for complete search history.

(56) References Cited

U.S. PATENT DOCUMENTS

| | | | |
|---|---|---|---|
| 4,280,233 A | | 7/1981 | Raab |
| 4,294,251 A | | 10/1981 | Greenwald et al. |
| 4,313,434 A | | 2/1982 | Segal |
| 4,341,691 A | | 7/1982 | Anuta |
| 4,369,772 A | | 1/1983 | Miller |
| 4,414,608 A | | 11/1983 | Furihata |
| 4,422,719 A | | 12/1983 | Orcutt |
| 4,433,898 A | | 2/1984 | Nasiri |
| 4,462,394 A | | 7/1984 | Jacobs |
| 4,466,435 A | | 8/1984 | Murray |
| 4,562,598 A | | 1/1986 | Kranz |
| 4,686,973 A | | 8/1987 | Frisch |
| 4,697,584 A | | 10/1987 | Haynes |
| 4,735,625 A | | 4/1988 | Davidson |
| 4,870,953 A | | 10/1989 | DonMicheal et al. |
| 4,888,024 A | | 12/1989 | Powlan |
| 4,892,550 A | | 1/1990 | Huebsch |
| 4,904,391 A | | 2/1990 | Freeman |
| 4,961,424 A | | 10/1990 | Kubota et al. |
| 4,963,151 A | | 10/1990 | Ducheyne et al. |
| 4,969,888 A | * | 11/1990 | Scholten et al. ................. 606/94 |
| 4,998,930 A | * | 3/1991 | Lundahl ........................ 606/15 |
| 5,019,075 A | * | 5/1991 | Spears et al. ...................... 606/7 |
| 5,030,093 A | | 7/1991 | Mitnick |
| 5,049,157 A | | 9/1991 | Mittelmeier et al. |
| 5,085,660 A | | 2/1992 | Lin |
| 5,092,899 A | | 3/1992 | Forte |
| 5,102,413 A | | 4/1992 | Poddar |
| 5,108,404 A | | 4/1992 | Scholten et al. |
| 5,112,333 A | | 5/1992 | Fixel |
| 5,207,669 A | | 5/1993 | Baker et al. |
| 5,222,958 A | | 6/1993 | Chin |
| 5,295,733 A | | 3/1994 | LeBegue |
| 5,295,962 A | | 3/1994 | Crocker et al. |
| 5,303,718 A | | 4/1994 | Krajicek |
| 5,316,550 A | | 5/1994 | Forte |
| 5,336,699 A | | 8/1994 | Cooke et al. |
| 5,372,598 A | | 12/1994 | Luhr et al. |
| 5,376,123 A | | 12/1994 | Klaue et al. |
| 5,391,144 A | | 2/1995 | Sakurai et al. |
| 5,415,654 A | | 5/1995 | Daikuzono |
| 5,423,850 A | * | 6/1995 | Berger .......................... 606/192 |
| 5,432,876 A | | 7/1995 | Appeldorn et al. |
| 5,443,468 A | | 8/1995 | Johnson |
| 5,445,608 A | | 8/1995 | Chen et al. |
| 5,462,552 A | | 10/1995 | Kiester |
| 5,480,400 A | | 1/1996 | Berger |
| 5,538,514 A | | 7/1996 | Hawkins |
| 5,548,676 A | | 8/1996 | Savage, Jr. |
| 5,554,111 A | | 9/1996 | Morrey et al. |
| 5,556,429 A | | 9/1996 | Felt |
| 5,571,204 A | | 11/1996 | Nies |
| 5,658,310 A | | 8/1997 | Berger |
| 5,658,963 A | | 8/1997 | Qian et al. |
| 5,705,181 A | | 1/1998 | Cooper et al. |
| 5,707,374 A | | 1/1998 | Schmidt |
| 5,713,901 A | | 2/1998 | Tock |
| 5,795,353 A | | 8/1998 | Felt |
| 5,824,087 A | | 10/1998 | Aspden et al. |
| 5,827,289 A | | 10/1998 | Reiley et al. |
| 5,888,220 A | | 3/1999 | Felt et al. |
| 5,891,082 A | * | 4/1999 | Leone et al. ..................... 604/21 |
| 5,897,557 A | | 4/1999 | Chin et al. |
| 5,908,433 A | | 6/1999 | Eager et al. |
| 5,930,424 A | | 7/1999 | Heimberger et al. |
| 5,972,015 A | | 10/1999 | Scribner et al. |
| 5,980,075 A | | 11/1999 | Sheaffer |
| 5,980,253 A | | 11/1999 | Oxman et al. |
| 5,987,199 A | | 11/1999 | Zarian et al. |
| 5,989,230 A | | 11/1999 | Frassica |
| 5,997,570 A | * | 12/1999 | Ligtenberg et al. ............ 607/92 |
| 6,008,264 A | | 12/1999 | Ostler |
| 6,019,761 A | | 2/2000 | Gustilo |
| 6,019,774 A | | 2/2000 | Weiss et al. |
| 6,033,411 A | | 3/2000 | Preissman |
| 6,039,762 A | | 3/2000 | McKay |
| 6,042,380 A | * | 3/2000 | De Rowe ....................... 433/173 |
| 6,048,346 A | | 4/2000 | Reiley et al. |
| 6,053,917 A | | 4/2000 | Sherman et al. |
| 6,059,789 A | | 5/2000 | Dinger et al. |
| 6,066,154 A | | 5/2000 | Reiley et al. |
| 6,077,265 A | | 6/2000 | Werding et al. |
| 6,079,868 A | | 6/2000 | Rydell |
| 6,103,203 A | | 8/2000 | Fischer |
| 6,110,176 A | | 8/2000 | Shapira |
| 6,121,341 A | | 9/2000 | Sawhney et al. |
| 6,127,597 A | | 10/2000 | Beyar et al. |
| 6,136,011 A | | 10/2000 | Stambaugh |
| 6,140,452 A | | 10/2000 | Felt et al. |
| 6,159,236 A | | 12/2000 | Biel |
| 6,179,852 B1 | | 1/2001 | Strickland et al. |
| 6,195,477 B1 | | 2/2001 | Denuto et al. |
| 6,200,134 B1 | | 3/2001 | Kovac et al. |
| 6,217,581 B1 | | 4/2001 | Tolson |
| 6,223,085 B1 | | 4/2001 | Dann et al. |
| 6,224,630 B1 | | 5/2001 | Bao et al. |
| 6,235,043 B1 | | 5/2001 | Reiley et al. |
| 6,241,734 B1 | | 6/2001 | Scribner et al. |
| 6,248,110 B1 | * | 6/2001 | Reiley et al. ................... 606/93 |
| 6,248,131 B1 | | 6/2001 | Felt et al. |
| 6,254,571 B1 | | 7/2001 | Hart |
| 6,258,089 B1 | | 7/2001 | Campbell et al. |
| 6,261,289 B1 | | 7/2001 | Levy |
| 6,280,456 B1 | | 8/2001 | Scribner et al. |
| 6,282,013 B1 | | 8/2001 | Ostler et al. |
| 6,290,382 B1 | | 9/2001 | Bourn et al. |
| 6,299,597 B1 | | 10/2001 | Buscemi et al. |
| 6,306,177 B1 | | 10/2001 | Felt et al. |
| 6,319,255 B1 | | 11/2001 | Grundei et al. |
| 6,332,894 B1 | | 12/2001 | Stalcup et al. |
| 6,336,914 B1 | | 1/2002 | Gillespie, III |
| 6,336,930 B1 | | 1/2002 | Stalcup et al. |
| 6,358,252 B1 | | 3/2002 | Shapira |
| 6,387,098 B1 | | 5/2002 | Cole et al. |
| 6,395,007 B1 | | 5/2002 | Bhatnagar et al. |
| 6,402,719 B1 | * | 6/2002 | Ponzi et al. ................ 604/95.04 |
| 6,416,531 B2 | | 7/2002 | Chen |
| 6,416,737 B1 | | 7/2002 | Manolagas et al. |
| 6,419,483 B1 | | 7/2002 | Adam et al. |
| 6,423,055 B1 | * | 7/2002 | Farr et al. ........................ 606/15 |
| 6,423,083 B2 | | 7/2002 | Reiley et al. |
| 6,425,923 B1 | | 7/2002 | Stalcup et al. |
| 6,440,444 B2 | | 8/2002 | Boyce et al. |
| 6,443,988 B2 | | 9/2002 | Felt et al. |
| 6,447,514 B1 | | 9/2002 | Stalcup et al. |

(56) References Cited

U.S. PATENT DOCUMENTS

| | | | |
|---|---|---|---|
| 6,458,375 B1 | 10/2002 | Gertzman et al. | |
| 6,478,751 B1 | 11/2002 | Krueger et al. | |
| 6,482,234 B1 | 11/2002 | Weber et al. | |
| 6,485,512 B1 | 11/2002 | Cheng | |
| 6,494,883 B1 | 12/2002 | Ferree | |
| 6,524,251 B2 | 2/2003 | Rabiner et al. | |
| 6,524,313 B1 | 2/2003 | Fassier et al. | |
| 6,551,321 B1 | 4/2003 | Burkinshaw et al. | |
| 6,551,337 B1 | 4/2003 | Rabiner et al. | |
| 6,565,528 B1 | 5/2003 | Mueller | |
| 6,579,277 B1 | 6/2003 | Rabiner et al. | |
| 6,579,279 B1 | 6/2003 | Rabiner et al. | |
| 6,605,056 B2 * | 8/2003 | Eidenschink et al. | 604/96.01 |
| 6,620,185 B1 | 9/2003 | Harvie et al. | |
| 6,623,505 B2 | 9/2003 | Scribner et al. | |
| 6,632,235 B2 | 10/2003 | Weikel et al. | |
| 6,648,881 B2 | 11/2003 | KenKnight et al. | |
| 6,652,547 B2 | 11/2003 | Rabiner et al. | |
| 6,652,587 B2 | 11/2003 | Felt et al. | |
| 6,660,013 B2 | 12/2003 | Rabiner et al. | |
| 6,679,873 B2 | 1/2004 | Rabiner et al. | |
| 6,695,781 B2 | 2/2004 | Rabiner et al. | |
| 6,695,782 B2 | 2/2004 | Rabiner et al. | |
| 6,696,073 B2 | 2/2004 | Boyce et al. | |
| 6,716,216 B1 * | 4/2004 | Boucher et al. | 606/86 R |
| 6,719,773 B1 * | 4/2004 | Boucher et al. | 606/192 |
| 6,726,691 B2 | 4/2004 | Osorio et al. | |
| 6,730,048 B1 | 5/2004 | Hare et al. | |
| 6,733,451 B2 | 5/2004 | Rabiner et al. | |
| 6,733,513 B2 | 5/2004 | Boyle et al. | |
| 6,740,093 B2 | 5/2004 | Hochschuler et al. | |
| 6,755,862 B2 | 6/2004 | Keynan | |
| 6,783,530 B1 | 8/2004 | Levy | |
| 6,802,835 B2 | 10/2004 | Rabiner et al. | |
| 6,818,018 B1 | 11/2004 | Sawhney | |
| 6,852,095 B1 * | 2/2005 | Ray | 604/93.01 |
| 6,866,678 B2 | 3/2005 | Shenderova et al. | |
| 6,869,442 B2 | 3/2005 | Cheng | |
| 6,875,212 B2 | 4/2005 | Shaolian et al. | |
| 6,885,246 B2 | 4/2005 | Tsutsui et al. | |
| 6,887,246 B2 | 5/2005 | Bhatnagar et al. | |
| 6,887,275 B2 | 5/2005 | Carchidi et al. | |
| 6,899,713 B2 | 5/2005 | Shaolian et al. | |
| 6,899,719 B2 | 5/2005 | Reiley et al. | |
| 6,932,843 B2 | 8/2005 | Smith et al. | |
| 6,964,667 B2 | 11/2005 | Shaolian et al. | |
| 6,975,898 B2 | 12/2005 | Seibel | |
| 6,979,341 B2 | 12/2005 | Scribner et al. | |
| 6,981,981 B2 | 1/2006 | Reiley et al. | |
| 7,001,431 B2 | 2/2006 | Bao et al. | |
| 7,008,433 B2 | 3/2006 | Voellmicke et al. | |
| 7,048,731 B2 | 5/2006 | Altshuler et al. | |
| 7,052,498 B2 | 5/2006 | Levy et al. | |
| 7,077,865 B2 | 7/2006 | Bao et al. | |
| 7,124,067 B2 | 10/2006 | Ascenzi | |
| 7,141,061 B2 | 11/2006 | Williams et al. | |
| 7,144,414 B2 | 12/2006 | Harvie et al. | |
| 7,153,305 B2 | 12/2006 | Johnson et al. | |
| 7,156,861 B2 | 1/2007 | Scribner et al. | |
| 7,156,880 B2 | 1/2007 | Evans et al. | |
| 7,169,140 B1 | 1/2007 | Kume | |
| 7,215,863 B1 | 5/2007 | Arenella et al. | |
| 7,241,303 B2 | 7/2007 | Reiss et al. | |
| 7,258,692 B2 | 8/2007 | Thelen et al. | |
| 7,261,720 B2 | 8/2007 | Stevens et al. | |
| 7,320,709 B2 | 1/2008 | Felt et al. | |
| 7,341,601 B2 | 3/2008 | Eisermann et al. | |
| 7,360,542 B2 | 4/2008 | Nelson et al. | |
| 7,407,616 B2 | 8/2008 | Melikechi et al. | |
| 7,419,450 B2 | 9/2008 | Ito | |
| 7,427,295 B2 | 9/2008 | Ellman et al. | |
| 7,465,318 B2 | 12/2008 | Sennett et al. | |
| 7,547,319 B2 | 6/2009 | Segal et al. | |
| 7,621,950 B1 | 11/2009 | Globerman et al. | |
| 7,628,800 B2 * | 12/2009 | Sherman et al. | 606/279 |
| 7,632,277 B2 | 12/2009 | Woll et al. | |
| 7,632,291 B2 | 12/2009 | Stephens et al. | |
| 7,666,205 B2 | 2/2010 | Weikel et al. | |
| 7,722,620 B2 | 5/2010 | Truckai et al. | |
| 7,740,656 B2 | 6/2010 | Mensah et al. | |
| 7,744,555 B2 | 6/2010 | DiMauro et al. | |
| 7,766,965 B2 | 8/2010 | Bao et al. | |
| 7,771,476 B2 | 8/2010 | Justis et al. | |
| 7,776,075 B2 | 8/2010 | Bruneau et al. | |
| 7,806,900 B2 | 10/2010 | Rabiner | |
| 7,811,284 B2 | 10/2010 | Rabiner | |
| 7,811,286 B2 | 10/2010 | Medoff | |
| 7,811,290 B2 | 10/2010 | Rabiner | |
| 7,842,040 B2 | 11/2010 | Rabiner et al. | |
| 7,850,711 B1 | 12/2010 | Stone et al. | |
| 7,857,748 B2 * | 12/2010 | Williams et al. | 600/36 |
| 7,879,041 B2 | 2/2011 | Rabiner et al. | |
| 7,912,539 B2 | 3/2011 | Doty et al. | |
| 7,947,015 B2 | 5/2011 | Herweck et al. | |
| 8,034,071 B2 | 10/2011 | Scribner et al. | |
| 8,123,807 B2 | 2/2012 | Kim et al. | |
| 8,187,278 B2 | 5/2012 | Biel | |
| 8,210,729 B2 | 7/2012 | O'Leary et al. | |
| 8,211,121 B1 | 7/2012 | Quinn et al. | |
| 8,246,628 B2 | 8/2012 | Rabiner | |
| 8,262,694 B2 | 9/2012 | Widomski et al. | |
| 8,328,402 B2 | 12/2012 | O'Leary et al. | |
| 8,348,956 B2 | 1/2013 | Rabiner | |
| 8,366,711 B2 | 2/2013 | Rabiner et al. | |
| 8,403,968 B2 | 3/2013 | Rabiner et al. | |
| 8,413,664 B2 | 4/2013 | Appling | |
| 8,512,338 B2 | 8/2013 | Rabiner et al. | |
| 8,545,499 B2 | 10/2013 | Lozier et al. | |
| 8,574,233 B2 | 11/2013 | Rabiner et al. | |
| 8,668,701 B2 | 3/2014 | Rabiner et al. | |
| 8,672,982 B2 | 3/2014 | Rabiner et al. | |
| 8,684,965 B2 | 4/2014 | Rabiner et al. | |
| 8,708,955 B2 * | 4/2014 | Tilson et al. | 604/103.1 |
| 8,734,460 B2 | 5/2014 | Rabiner et al. | |
| 8,764,761 B2 * | 7/2014 | Truckai et al. | 606/93 |
| 8,870,965 B2 | 10/2014 | Rabiner et al. | |
| 8,906,030 B2 | 12/2014 | Rabiner et al. | |
| 8,906,031 B2 | 12/2014 | Rabiner et al. | |
| 8,915,966 B2 | 12/2014 | Rabiner et al. | |
| 8,936,382 B2 | 1/2015 | O'Leary et al. | |
| 8,936,644 B2 | 1/2015 | Rabiner et al. | |
| 8,939,977 B2 | 1/2015 | DiPoto et al. | |
| 9,005,254 B2 | 4/2015 | Rabiner et al. | |
| 9,050,079 B2 | 6/2015 | Rabiner et al. | |
| 9,101,419 B2 | 8/2015 | Colleran et al. | |
| 9,125,706 B2 | 9/2015 | Rabiner et al. | |
| 9,144,442 B2 | 9/2015 | Rabiner et al. | |
| 9,179,959 B2 | 11/2015 | Rabiner et al. | |
| 9,216,049 B2 | 12/2015 | Rabiner et al. | |
| 9,254,156 B2 | 2/2016 | Rabiner | |
| 9,254,195 B2 | 2/2016 | Rabiner et al. | |
| 9,265,549 B2 | 2/2016 | Rabiner | |
| 9,427,289 B2 | 8/2016 | Rabiner et al. | |
| 9,433,450 B2 | 9/2016 | Rabiner et al. | |
| 2001/0011174 A1 | 8/2001 | Reiley et al. | |
| 2001/0044626 A1 | 11/2001 | Reiley et al. | |
| 2001/0055462 A1 | 12/2001 | Seibel | |
| 2002/0032444 A1 | 3/2002 | Mische | |
| 2002/0082600 A1 | 6/2002 | Shaolian et al. | |
| 2002/0091424 A1 | 7/2002 | Biel | |
| 2002/0156482 A1 | 10/2002 | Scribner et al. | |
| 2002/0161373 A1 * | 10/2002 | Osorio et al. | 606/86 |
| 2002/0165544 A1 | 11/2002 | Perren et al. | |
| 2002/0198526 A1 | 12/2002 | Shaolian et al. | |
| 2003/0028210 A1 | 2/2003 | Boyle et al. | |
| 2003/0083642 A1 | 5/2003 | Boyd et al. | |
| 2003/0105469 A1 | 6/2003 | Karmon | |
| 2003/0114914 A1 * | 6/2003 | Cheng | 623/1.11 |
| 2003/0156431 A1 | 8/2003 | Gozum et al. | |
| 2003/0199850 A1 | 10/2003 | Chavez et al. | |
| 2003/0212426 A1 | 11/2003 | Olson et al. | |
| 2003/0229372 A1 * | 12/2003 | Reiley et al. | 606/192 |
| 2004/0006341 A1 | 1/2004 | Shaolian et al. | |
| 2004/0024388 A1 | 2/2004 | Altshuler | |

(56) References Cited

U.S. PATENT DOCUMENTS

| | | |
|---|---|---|
| 2004/0034434 A1 | 2/2004 | Evans et al. |
| 2004/0059333 A1 | 3/2004 | Carl et al. |
| 2004/0059417 A1 | 3/2004 | Smith et al. |
| 2004/0092948 A1 | 5/2004 | Stevens et al. |
| 2004/0098015 A1 | 5/2004 | Weikel et al. |
| 2004/0117025 A1 | 6/2004 | Reindel |
| 2004/0133280 A1 | 7/2004 | Trieu |
| 2004/0167561 A1 | 8/2004 | Boucher et al. |
| 2004/0167625 A1 | 8/2004 | Beyar et al. |
| 2004/0225296 A1 | 11/2004 | Reiss et al. |
| 2004/0228142 A1 | 11/2004 | Takada et al. |
| 2004/0230193 A1* | 11/2004 | Cheung et al. ............... 606/63 |
| 2004/0230309 A1 | 11/2004 | Di Mauro et al. |
| 2004/0236366 A1 | 11/2004 | Kennedy |
| 2004/0247641 A1 | 12/2004 | Felt et al. |
| 2005/0010231 A1 | 1/2005 | Myers |
| 2005/0010297 A1 | 1/2005 | Watson et al. |
| 2005/0015140 A1 | 1/2005 | deBeer |
| 2005/0015148 A1 | 1/2005 | Jansen et al. |
| 2005/0018989 A1* | 1/2005 | Shimizu ............... G02B 6/1221 385/129 |
| 2005/0033437 A1 | 2/2005 | Bao et al. |
| 2005/0043733 A1 | 2/2005 | Eisermann et al. |
| 2005/0043808 A1* | 2/2005 | Felt et al. ............... 623/20.14 |
| 2005/0049691 A1 | 3/2005 | Mericle et al. |
| 2005/0090901 A1 | 4/2005 | Studer |
| 2005/0119662 A1 | 6/2005 | Reiley et al. |
| 2005/0142315 A1 | 6/2005 | DeSimone et al. |
| 2005/0149022 A1 | 7/2005 | Shaolian et al. |
| 2005/0159749 A1 | 7/2005 | Levy et al. |
| 2005/0171604 A1 | 8/2005 | Michalow |
| 2005/0192671 A1 | 9/2005 | Bao et al. |
| 2005/0197711 A1 | 9/2005 | Cachia |
| 2005/0228260 A1* | 10/2005 | Burwell et al. ............... 600/408 |
| 2005/0234453 A1 | 10/2005 | Shaolian et al. |
| 2005/0251140 A1 | 11/2005 | Shaolian et al. |
| 2005/0284485 A9 | 12/2005 | Nelson et al. |
| 2006/0009550 A1 | 1/2006 | Messersmith et al. |
| 2006/0015105 A1 | 1/2006 | Warren et al. |
| 2006/0036253 A1 | 2/2006 | Leroux et al. |
| 2006/0084985 A1 | 4/2006 | Kim et al. |
| 2006/0100547 A1 | 5/2006 | Rabiner et al. |
| 2006/0100635 A1 | 5/2006 | Reiley et al. |
| 2006/0100706 A1 | 5/2006 | Shadduck et al. |
| 2006/0111726 A1 | 5/2006 | Felt et al. |
| 2006/0122625 A1 | 6/2006 | Truckai et al. |
| 2006/0142747 A1 | 6/2006 | Appling |
| 2006/0155296 A1* | 7/2006 | Richter ............... 606/94 |
| 2006/0173464 A1 | 8/2006 | Ellman et al. |
| 2006/0183811 A1 | 8/2006 | Melikechi et al. |
| 2006/0184246 A1 | 8/2006 | Zwirkoski |
| 2006/0195165 A1 | 8/2006 | Gertner et al. |
| 2006/0217747 A1 | 9/2006 | Ferree |
| 2006/0229617 A1 | 10/2006 | Meller et al. |
| 2006/0229625 A1 | 10/2006 | Truckai et al. |
| 2006/0247787 A1 | 11/2006 | Rydell et al. |
| 2006/0253102 A1 | 11/2006 | Nance et al. |
| 2006/0253200 A1 | 11/2006 | Bao et al. |
| 2006/0258981 A1 | 11/2006 | Eidenschink |
| 2006/0264950 A1 | 11/2006 | Nelson et al. |
| 2006/0264951 A1 | 11/2006 | Nelson et al. |
| 2006/0264952 A1 | 11/2006 | Nelson et al. |
| 2006/0265077 A1 | 11/2006 | Zwirkoski |
| 2006/0271024 A1 | 11/2006 | Gertner et al. |
| 2006/0271061 A1 | 11/2006 | Beyar et al. |
| 2006/0276793 A1 | 12/2006 | Berry |
| 2006/0276819 A1 | 12/2006 | Osorio et al. |
| 2006/0282169 A1 | 12/2006 | Felt et al. |
| 2006/0287730 A1 | 12/2006 | Segal et al. |
| 2007/0027547 A1 | 2/2007 | Rydell et al. |
| 2007/0067032 A1 | 3/2007 | Felt et al. |
| 2007/0087031 A1 | 4/2007 | Ashman et al. |
| 2007/0100327 A1 | 5/2007 | Smith |
| 2007/0104416 A1* | 5/2007 | Shimizu ............ B29D 11/00663 385/14 |
| 2007/0118143 A1 | 5/2007 | Ralph et al. |
| 2007/0123876 A1 | 5/2007 | Czartoski et al. |
| 2007/0123877 A1* | 5/2007 | Goldin et al. ............... 606/62 |
| 2007/0123878 A1 | 5/2007 | Shaver et al. |
| 2007/0161991 A1 | 7/2007 | Altarac et al. |
| 2007/0198023 A1 | 8/2007 | Sand et al. |
| 2007/0225705 A1 | 9/2007 | Osorio et al. |
| 2007/0233146 A1 | 10/2007 | Henniges et al. |
| 2007/0239148 A1 | 10/2007 | Scheller |
| 2007/0250062 A1* | 10/2007 | Ara Pinilla et al. ............ 606/62 |
| 2007/0255287 A1 | 11/2007 | Rabiner |
| 2008/0015500 A1 | 1/2008 | Herweck et al. |
| 2008/0021474 A1 | 1/2008 | Bonutti et al. |
| 2008/0039854 A1 | 2/2008 | Rabiner |
| 2008/0080205 A1 | 4/2008 | Forrester et al. |
| 2008/0103505 A1* | 5/2008 | Fransen ............... 606/92 |
| 2008/0125784 A1* | 5/2008 | Rabiner ............... A61B 17/68 606/92 |
| 2008/0154368 A1 | 6/2008 | Justis |
| 2008/0154373 A1* | 6/2008 | Protopsaltis et al. ...... 623/17.12 |
| 2008/0183122 A1 | 7/2008 | Fisher et al. |
| 2008/0188805 A1* | 8/2008 | Davies et al. ............ 604/103.06 |
| 2008/0188858 A1 | 8/2008 | Luzzi et al. |
| 2008/0234820 A1 | 9/2008 | Felt et al. |
| 2008/0249529 A1 | 10/2008 | Zarda et al. |
| 2008/0255560 A1 | 10/2008 | Myers et al. |
| 2008/0269750 A1 | 10/2008 | Justin |
| 2008/0287951 A1 | 11/2008 | Stoneburner et al. |
| 2008/0308753 A1 | 12/2008 | Stuba et al. |
| 2009/0005782 A1 | 1/2009 | Chirico et al. |
| 2009/0018524 A1 | 1/2009 | Greenhalgh et al. |
| 2009/0024166 A1 | 1/2009 | Carl et al. |
| 2009/0048629 A1 | 2/2009 | Rabiner |
| 2009/0054900 A1 | 2/2009 | Rabiner et al. |
| 2009/0076610 A1 | 3/2009 | Afzal et al. |
| 2009/0093887 A1 | 4/2009 | Walter et al. |
| 2009/0112196 A1 | 4/2009 | Rabiner et al. |
| 2009/0118833 A1 | 5/2009 | Hudgins et al. |
| 2009/0125028 A1* | 5/2009 | Teisen ............... A61B 17/68 606/63 |
| 2009/0171265 A1 | 7/2009 | Doty et al. |
| 2009/0171358 A1 | 7/2009 | Chang et al. |
| 2009/0177204 A1 | 7/2009 | Colleran et al. |
| 2009/0182336 A1* | 7/2009 | Brenzel ............... A61B 17/7225 606/62 |
| 2009/0187192 A1* | 7/2009 | Rabiner et al. ............... 606/93 |
| 2009/0216232 A1 | 8/2009 | Buford, III et al. |
| 2009/0228007 A1 | 9/2009 | Justin et al. |
| 2009/0254064 A1 | 10/2009 | Boatman |
| 2009/0287309 A1 | 11/2009 | Walch et al. |
| 2009/0306589 A1* | 12/2009 | Tilson et al. ............... 604/103.1 |
| 2010/0076503 A1 | 3/2010 | Beyar et al. |
| 2010/0234958 A1 | 9/2010 | Linares |
| 2010/0241178 A1 | 9/2010 | Tilson et al. ............... 606/86 R |
| 2010/0249942 A1 | 9/2010 | Goswami et al. |
| 2010/0256641 A1 | 10/2010 | Rabiner et al. |
| 2010/0262069 A1 | 10/2010 | Rabiner et al. |
| 2010/0262188 A1 | 10/2010 | Rabiner et al. |
| 2010/0265733 A1 | 10/2010 | O'Leary et al. |
| 2010/0318087 A1 | 12/2010 | Scribner et al. |
| 2010/0331850 A1 | 12/2010 | Rabiner |
| 2011/0004213 A1 | 1/2011 | Rabiner et al. |
| 2011/0009871 A1 | 1/2011 | Rabiner |
| 2011/0029093 A1 | 2/2011 | Bojarski et al. |
| 2011/0046746 A1 | 2/2011 | Rabiner et al. |
| 2011/0077651 A1 | 3/2011 | Lozier et al. |
| 2011/0082504 A1* | 4/2011 | Singhatat et al. ............ 606/249 |
| 2011/0098713 A1 | 4/2011 | Rabiner et al. |
| 2011/0110114 A1 | 5/2011 | Papac et al. |
| 2011/0112588 A1* | 5/2011 | Linderman et al. ......... 606/86 R |
| 2011/0118740 A1 | 5/2011 | Rabiner et al. |
| 2011/0137137 A1* | 6/2011 | O'Halloran et al. ............ 606/92 |
| 2011/0160870 A1 | 6/2011 | Baumgartner et al. |
| 2011/0166306 A1 | 7/2011 | Stansbury et al. |
| 2011/0218626 A1* | 9/2011 | Krinke et al. ............ 623/16.11 |
| 2011/0268866 A1 | 11/2011 | Parker |
| 2011/0288522 A1 | 11/2011 | Hollowel et al. |
| 2011/0313356 A1 | 12/2011 | Rabiner et al. |
| 2012/0016371 A1 | 1/2012 | O'Halloran et al. |

(56) References Cited

U.S. PATENT DOCUMENTS

| | | |
|---|---|---|
| 2012/0022540 A1 | 1/2012 | Chasmawala et al. |
| 2012/0029102 A1* | 2/2012 | Rose et al. ............... 521/88 |
| 2012/0041557 A1* | 2/2012 | Frigg .................. 623/16.11 |
| 2012/0165941 A1 | 6/2012 | Rabiner et al. |
| 2012/0259375 A1 | 10/2012 | Druma et al. |
| 2012/0262939 A1 | 10/2012 | O'Leary et al. |
| 2012/0289968 A1 | 11/2012 | Rabiner |
| 2012/0316652 A1* | 12/2012 | Renganath et al. ....... 623/17.16 |
| 2013/0003406 A1 | 1/2013 | O'Leary et al. |
| 2013/0006304 A1 | 1/2013 | Rabiner et al. |
| 2013/0012998 A1 | 1/2013 | Altarac et al. |
| 2013/0013008 A1 | 1/2013 | Rabiner et al. |
| 2013/0013009 A1 | 1/2013 | Colleran et al. |
| 2013/0013010 A1 | 1/2013 | Rabiner et al. |
| 2013/0018482 A1 | 1/2013 | Meridew et al. |
| 2013/0023876 A1 | 1/2013 | Rabiner et al. |
| 2013/0023877 A1 | 1/2013 | Rabiner et al. |
| 2013/0041472 A1 | 2/2013 | Rabiner et al. |
| 2013/0046390 A1 | 2/2013 | Rabiner et al. |
| 2013/0066326 A1 | 3/2013 | Rabiner et al. |
| 2013/0158607 A1 | 6/2013 | Rabiner et al. |
| 2013/0184715 A1 | 7/2013 | Rabiner et al. |
| 2013/0310875 A1 | 11/2013 | Rabiner et al. |
| 2014/0018806 A1 | 1/2014 | DiPoto et al. |
| 2014/0135847 A1 | 5/2014 | Rabiner et al. |
| 2014/0142581 A1 | 5/2014 | Rabiner et al. |
| 2014/0148813 A1 | 5/2014 | Rabiner et al. |
| 2014/0163453 A1 | 6/2014 | Rabiner et al. |
| 2014/0180288 A1 | 6/2014 | Rabiner et al. |
| 2015/0066028 A1 | 3/2015 | Rabiner et al. |
| 2015/0066085 A1 | 3/2015 | Rabiner et al. |
| 2015/0080900 A1 | 3/2015 | Rabiner et al. |
| 2015/0088268 A1 | 3/2015 | Rabiner et al. |
| 2015/0374498 A1 | 12/2015 | Rabiner et al. |
| 2016/0022333 A1 | 1/2016 | Rabiner et al. |
| 2016/0128750 A1 | 5/2016 | Rabiner et al. |
| 2016/0128836 A1 | 5/2016 | Rabiner et al. |

FOREIGN PATENT DOCUMENTS

| | | |
|---|---|---|
| EP | 2 298 201 | 3/2011 |
| JP | 2001-527437 | 12/2001 |
| JP | 2004-526525 | 9/2002 |
| JP | 2005-511143 | 4/2005 |
| JP | 2006-212425 | 8/2006 |
| NL | 9001858 | 3/1992 |
| WO | WO 98/38918 | 9/1998 |
| WO | WO9943266 | 9/1999 |
| WO | WO 02/30338 A1 | 4/2002 |
| WO | WO 02/43628 | 6/2002 |
| WO | WO 03/047472 | 6/2003 |
| WO | WO 2004/045393 | 6/2004 |
| WO | WO 2004/058045 | 7/2004 |
| WO | WO 2004/073563 | 9/2004 |
| WO | WO 2004/112661 | 12/2004 |
| WO | 2005102224 | 11/2005 |
| WO | WO 2005/112804 | 12/2005 |
| WO | WO 2006/016807 | 2/2006 |
| WO | WO2007002251 | 1/2007 |
| WO | WO 2007/059259 | 5/2007 |
| WO | WO 2007/075375 | 7/2007 |
| WO | WO 2007/127255 | 11/2007 |
| WO | WO 2007/127260 | 11/2007 |
| WO | 2008021972 | 2/2008 |
| WO | WO 2008/039811 | 4/2008 |
| WO | WO 2008/063265 | 5/2008 |
| WO | 2008096363 | 8/2008 |
| WO | WO 2009/059090 | 5/2009 |
| WO | WO 2009/064847 | 5/2009 |
| WO | 2009091811 | 7/2009 |
| WO | WO 2009/082688 | 7/2009 |
| WO | WO2009088927 | 7/2009 |
| WO | WO 2009/131999 | 10/2009 |
| WO | WO 2010/050965 | 5/2010 |
| WO | WO 2010/118158 | 10/2010 |
| WO | WO 2011/060062 | 5/2011 |
| WO | 2011066522 | 6/2011 |
| WO | WO 2011/071567 | 6/2011 |
| WO | WO 2011/162910 | 12/2011 |
| WO | WO2011162910 | 12/2011 |
| WO | 2012050583 | 4/2012 |
| WO | WO2012051312 | 4/2012 |
| WO | WO 2012/088432 | 6/2012 |
| WO | WO 2013/013069 | 1/2013 |
| WO | WO 2013/013071 | 1/2013 |
| WO | WO 2013/013072 | 1/2013 |
| WO | WO2013/059609 | 4/2013 |
| WO | WO2014011669 | 1/2014 |

OTHER PUBLICATIONS

USPTO Office Action in U.S. Appl. No. 12/859,680 mailed Jul. 9, 2013.
USPTO Office Action in U.S. Appl. No. 13/561,249 mailed Sep. 16, 2013.
USPTO Office Action in U.S. Appl. No. 13/088,916 mailed Sep. 17, 2013.
USPTO Office Action in U.S. Appl. No. 12/943,544 mailed Sep. 25, 2013.
USPTO Office Action in U.S. Appl. No. 13/617,557 mailed Oct. 9, 2013.
Extended European Search Report based on EP 10 76 2390 dated Oct. 30, 2013.
USPTO Office Action in U.S. Appl. No. 12/262,370 mailed Nov. 21, 2013.
USPTO Office Action in U.S. Appl. No. 12/859,680 mailed Nov. 9, 2012.
USPTO Office Action in U.S. Appl. No. 12/943,544 mailed Dec. 3, 2012.
USPTO Office Action in U.S. Appl. No. 12/859,680 mailed Jan. 17, 2013.
USPTO Office Action in U.S. Appl. No. 12/262,370 mailed Dec. 14, 2012.
International Search Report and Written Opinion for PCT/US2012/061047 mailed Jan. 7, 2013.
USPTO Office Action in U.S. Appl. No. 12/756,014 mailed Jan. 22, 2013.
USPTO Office Action in U.S. Appl. No. 13/088,916 mailed Jan. 23, 2013.
Jovanovic et al., "Fixion Nails for Humeral Fractures, Injury", Int. J. Care Injured, vol. 35, Issue 11, pp. 1140-1142, Nov. 2004.
Maruyama et al., "Metacarpal Fracture Fixation with Absorbable Polyglycolide Rods and Stainless Steel K Wires: A Biomechanical Comparison", Journal of Biomedical Materials Research (Applied Biomaterials), vol. 33, Issue 1, pp. 9-12, Apr. 1996.
Waris et al., "Bioabsorbable Miniplating Versus Metallic Fixation for Metacarpal Fractures", Clinical Orthopaedics and Related Research, No. 410, pp. 310-319, May 2003.
Waris et al., "Self-Reinforced Bioabsorbable Versus Metallic Fixation Systems for Metacarpal and Phalangeal Fractures: A Biomechanical Study", The Journal of Hand Surgery, vol. 27A, No. 5, pp. 902-909, Sep. 2002.
PCT International Search Report based on PCT/US07/20402 dated Apr. 1, 2008.
PCT International Search Report based on PCT/US07/10050 dated Apr. 17, 2008.
PCT International Search Report based on PCT/US07/10038 dated Aug. 27, 2008.
PCT International Search Report based on PCT/US08/81929 dated Jan. 12, 2009.
PCT International Search Report based on PCT/US08/81924 dated Feb. 9, 2009.
PCT International Search Report based on PCT/US08/87630 dated Feb. 24, 2009.
PCT International Search Report based on PCT/US10/30275 dated Aug. 11, 2010.
PCT International Search Report based on PCT/US10/56219 dated Jan. 20, 2011.

(56) References Cited

OTHER PUBLICATIONS

PCT International Search Report based on PCT/US10/46003 dated May 24, 2011.
PCT International Search Report based on PCT/US11/38389 dated Sep. 22, 2011.
PCT International Search Report based on PCT/US11/66871 dated May 1, 2012.
USPTO Office Action in U.S. Appl. No. 11/789,906 mailed Apr. 29, 2009.
USPTO Office Action in U.S. Appl. No. 11/789,906 mailed Mar. 11, 2010.
USPTO Office Action in U.S. Appl. No. 11/789,906 mailed Apr. 30, 2010.
USPTO Office Action in U.S. Appl. No. 11/789,907 mailed May 11, 2010.
USPTO Office Action in U.S. Appl. No. 11/903,123 mailed Jul. 1, 2010.
USPTO Office Action in U.S. Appl. No. 11/964,370 mailed Dec. 9, 2010.
USPTO Office Action in U.S. Appl. No. 11/964,370 mailed Apr. 28, 2011.
USPTO Office Action in U.S. Appl. No. 11/964,370 mailed Sep. 23, 2011.
USPTO Office Action in U.S. Appl. No. 11/964,370 mailed Mar. 16, 2012.
USPTO Office Action in U.S. Appl. No. 12/262,411 mailed Sep. 1, 2010.
USPTO Office Action in U.S. Appl. No. 12/755,784 mailed Dec. 23, 2011.
USPTO Office Action in U.S. Appl. No. 12/756,014 mailed May 11, 2012.
USPTO Office Action in U.S. Appl. No. 12/858,924 mailed Oct. 24, 2011.
USPTO Office Action in U.S. Appl. No. 12/858,924 mailed Apr. 4, 2012.
USPTO Office Action in U.S. Appl. No. 12/875,460 mailed Mar. 8, 2012.
USPTO Office Action in U.S. Appl. No. 12/886,288 mailed Dec. 27, 2011.
USPTO Office Action in U.S. Appl. No. 12/262,370 mailed May 29, 2012.
USPTO Office Action in U.S. Appl. No. 12/943,544 mailed Jun. 8, 2012.
USPTO Office Action in U.S. Appl. No. 12/886,288 mailed Jun. 26, 2012.
USPTO Office Action in U.S. Appl. No. 11/964,370 mailed Jul. 6, 2012.
Extended European Search Report based on EP 07 75 6022 dated Jul. 30, 2012.
Extended European Search Report based on EP 07 75 6016 dated Jul. 30, 2012.
USPTO Office Action in U.S. Appl. No. 12/755,784 mailed Aug. 1, 2012.
USPTO Office Action in U.S. Appl. No. 12/858,924 mailed Aug. 2, 2012.
USPTO Office Action in U.S. Appl. No. 12/886,288 mailed Aug. 15, 2012.
PCT International Search Report based on PCT/US12/47447 dated Oct. 2, 2012.
PCT International Search Report based on PCT/US12/47446 dated Oct. 15, 2012.
PCT International Search Report based on PCT/US12/47444 dated Oct. 18, 2012.
USPTO Office Action in U.S. Appl. No. 12/756,014 mailed Oct. 25, 2012.
Supplemental European Search Report based on EP 08 87 7881 dated May 15, 2013.
USPTO Office Action in U.S. Appl. No. 13/617,557 mailed Feb. 4, 2013.
USPTO Office Action in U.S. Appl. No. 12/755,784 mailed Mar. 13, 2013.
USPTO Office Action in U.S. Appl. No. 13/616,416 mailed Mar. 25, 2013.
USPTO Office Action in U.S. Appl. No. 13/561,249 mailed Apr. 23, 2013.
USPTO Office Action in U.S. Appl. No. 12/262,370 mailed Apr. 26, 2013.
USPTO Office Action in U.S. Appl. No. 13/088,916 mailed May 13, 2013.
USPTO Office Action in U.S. Appl. No. 12/983,496 mailed Feb. 5, 2014.
USPTO Office Action in U.S. Appl. No. 12/756,014 mailed Feb. 13, 2014.
USPTO Office Action in U.S. Appl. No. 13/617,181 mailed Feb. 25, 2014.
PCT International Search Report based on PCT/US13/076598 dated Mar. 19, 2014.
USPTO Office Action in U.S. Appl. No. 13/655,808 mailed Mar. 27, 2014.
Extended European Search Report based on EP 14156473 dated May 13, 2014.
USPTO Office Action in U.S. Appl. No. 13/800,518 mailed Jun. 10, 2014.
USPTO Office Action in U.S. Appl. No. 12/262,370 mailed Jun. 26, 2014.
USPTO Office Action in U.S. Appl. No. 13/617,557 mailed Jun. 27, 2014.
PCT International Search Report based on PCT/US13/049773 dated Oct. 1, 2013.
USPTO Office Action in U.S. Appl. No. 12/756,014 mailed Oct. 7, 2014.
USPTO Office Action in U.S. Appl. No. 13/553,450 mailed Oct. 24, 2014.
USPTO Office Action in U.S. Appl. No. 13/335,110 mailed Oct. 24, 2014.
USPTO Office Action in U.S. Appl. No. 13/553,051 mailed Dec. 23, 2014.
USPTO Office Action in U.S. Appl. No. 12/262,370 mailed Jan. 14, 2015.
USPTO Office Action in U.S. Appl. No. 13/617,557 mailed Jan. 15, 2015.
USPTO Office Action in U.S. Appl. No. 13/335,110 mailed Feb. 9, 2015.
USPTO Office Action in U.S. Appl. No. 13/796,085 mailed Feb. 12, 2015.
USPTO Office Action in U.S. Appl. No. 13/553,051 mailed Mar. 31, 2015.
USPTO Office Action in U.S. Appl. No. 13/297,097 mailed May 29, 2015.
USPTO Office Action in U.S. Appl. No. 14/171,036 mailed Jun. 1, 2015.
USPTO Office Action in U.S. Appl. No. 14/164,846 mailed Jun. 4, 2015.
USPTO Office Action in U.S. Appl. No. 13/617,557 mailed Jul. 15, 2015.
USPTO Office Action in U.S. Appl. No. 13/796,085 mailed Jul. 17 2015.
USPTO Office Action in U.S. Appl. No. 13/553,051 mailed Sep. 11, 2015.
USPTO Office Action in U.S. Appl. No. 14/164,846 mailed Oct. 14, 2015.
USPTO Office Action in U.S. Appl. No. 14/171,036 mailed Oct. 15, 2015.
USPTO Office Action in U.S. Appl. No. 12/262,370 mailed Oct. 22, 2015.
USPTO Office Action in U.S. Appl. No. 13/796,085 mailed Nov. 27, 2015.
USPTO Office Action in U.S. Appl. No. 12/262,370 mailed Jun. 2, 2016.
USPTO Office Action in U.S. Appl. No. 13/796,085 mailed Jul. 1, 2016.

(56) References Cited

OTHER PUBLICATIONS

USPTO Office Action in U.S. Appl. No. 13/553,051 mailed Jan. 6, 2016.
USPTO Office Action in U.S. Appl. No. 13/617,557 mailed Jan. 14, 2016.
USPTO Office Action in U.S. Appl. No. 14/177,748 mailed Jan. 25, 2016.
USPTO Office Action in U.S. Appl. No. 14/535,913 mailed Feb. 22, 2016.
USPTO Office Action in U.S. Appl. No. 14/535,971 mailed Mar. 4, 2016.
USPTO Office Action in U.S. Appl. No. 14/535,913 mailed Sep. 26, 2016.
USPTO Office Action in U.S. Appl. No. 14/996,275 mailed Nov. 14, 2016.
International Search Report in PCT/US2016/60603 mailed Jan. 30, 2017.
U.S. Appl. No. 13/796,085, filed Mar. 12, 2013, Distal Tip for Bone Fixation Devices, Robert, Eduardo C.
U.S. Appl. No. 14/163,027, filed Jan. 24, 2014, Methods for Repairing Craniomaxillofacial Bones Using Customized Bone Plates, Hanna, Samuel Saleeb.
U.S. Appl. No. 14/164,846, filed Jan. 27, 2014, Apparatus for Delivery of Reinforcing Materials to Bone, Philogene, Pedro.
U.S. Appl. No. 14/171,036, filed Feb. 2, 2014, Apparatus for Delivery of Reinforcing Materials to Bone, Philogene, Pedro.
U.S. Appl. No. 14/177,748, filed Feb. 11, 2014, Photodynamic Bone Stabilization and Drug Delivery Systems.

\* cited by examiner

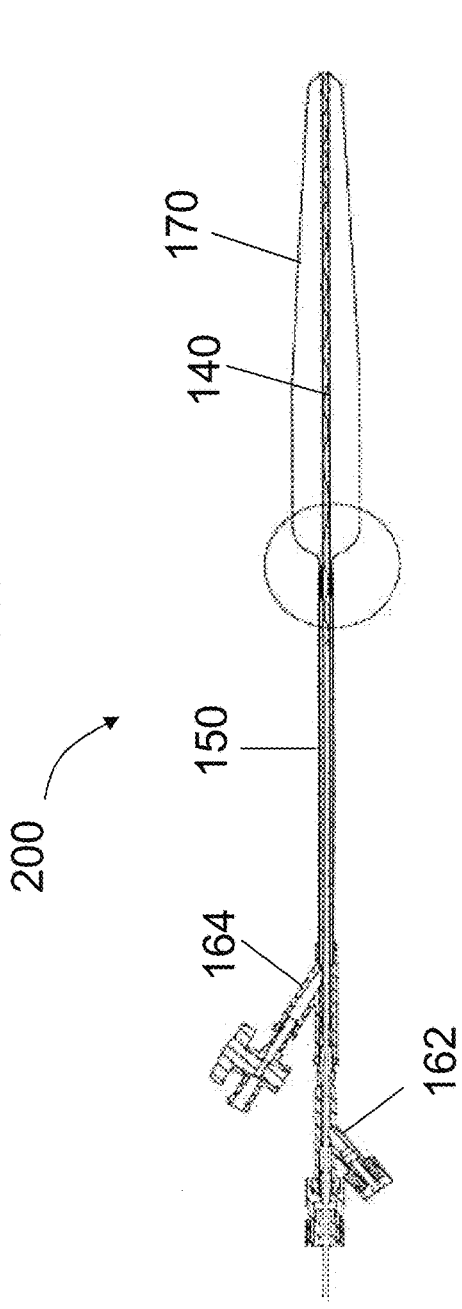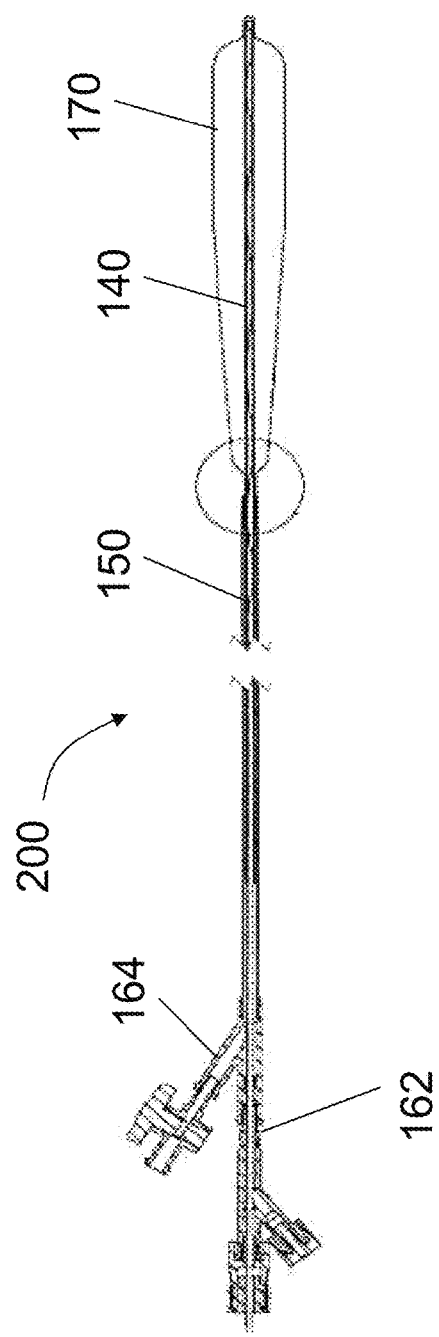

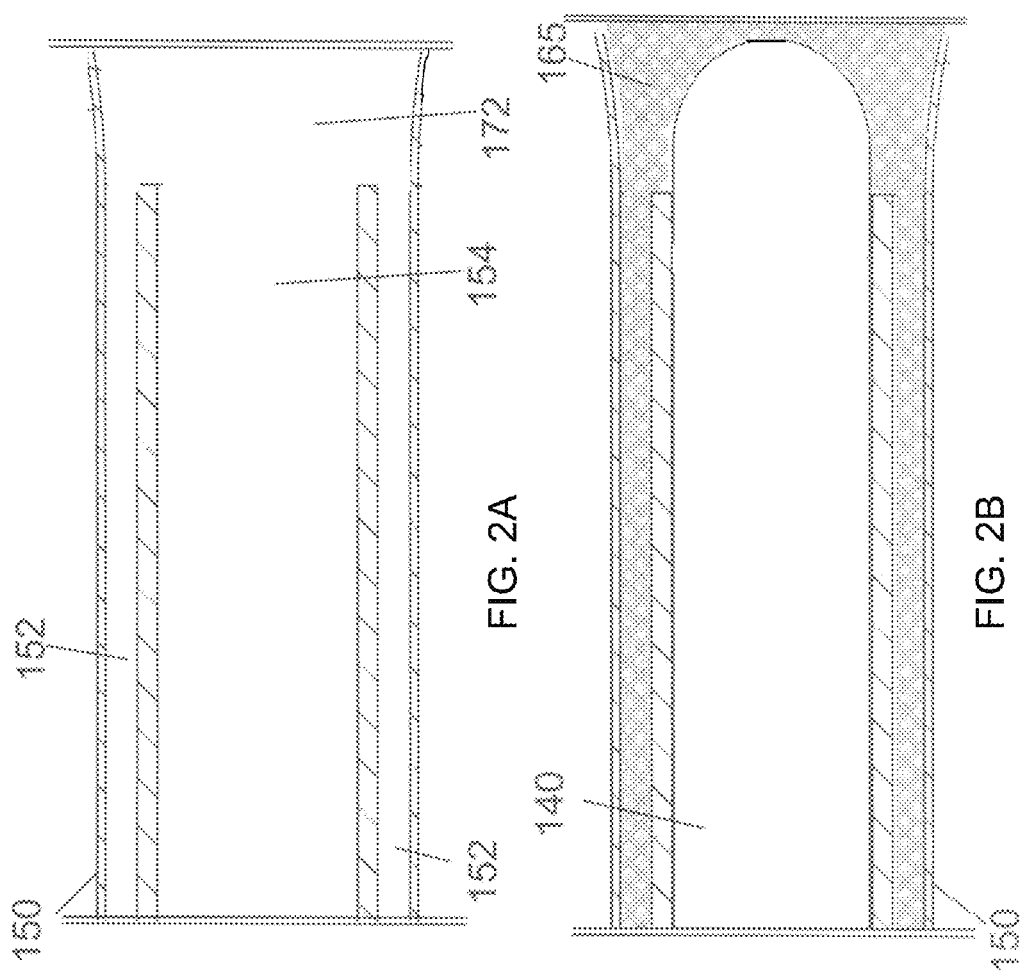

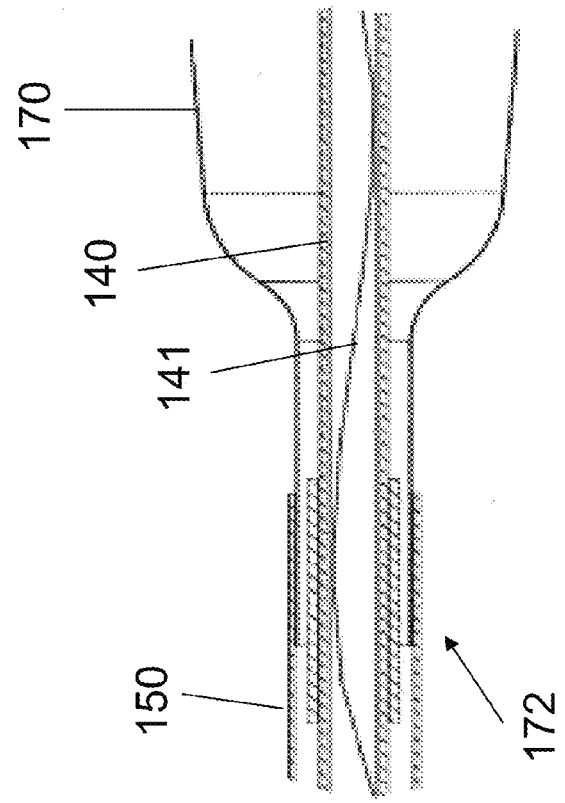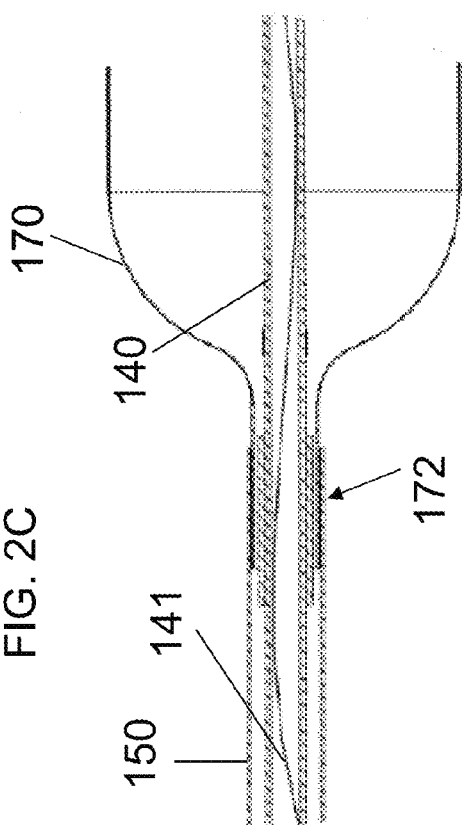

DEVICES AND METHODS FOR BONE RESTRUCTURE AND STABILIZATION

RELATED APPLICATIONS

This application claims the benefit of and priority to U.S. Provisional Patent Application No. 61/509,391, filed on Jul. 19, 2011, U.S. Provisional Patent Application No. 61/509,314, filed on Jul. 19, 2011, and U.S. Provisional Patent Application No. 61/509,459, filed on Jul. 19, 2011, the entirety of these applications are hereby incorporated herein by reference.

FIELD

The embodiments disclosed herein relate to bone implants, and more particularly to devices and methods for bone restructure and stabilization.

BACKGROUND

Bones form the skeleton of the body and allow the body to be supported against gravity and to move and function in the world. Bone fractures can occur, for example, from an outside force or from a controlled surgical cut (an osteotomy). A fracture's alignment is described as to whether the fracture fragments are displaced or in their normal anatomic position. In some instances, surgery may be required to re-align and stabilize the fractured bone. But proper positioning and alignment of a bone is difficult to achieve. It would be desirable to have an improved device or method for stabilizing, positioning, and repairing a fractured or weakened bone.

SUMMARY

Devices and methods for bone restructure and stabilization are disclosed herein. According to aspects illustrated herein, there is provided a device for repairing or stabilizing a fractured or weakened head of a bone that includes a delivery catheter having an elongated shaft with a proximal end, a distal end, and a longitudinal axis therebetween, the delivery catheter having an inner void for passing at least one light sensitive liquid, and an inner lumen; an expandable member releasably engaging the distal end of the delivery catheter, the expandable member moving from a deflated state to an inflated state when the at least one light sensitive liquid is passed to the expandable member, wherein the expandable member is sufficiently designed to be at least partially placed into a space within a head of a bone; and a light conducting fiber sized to pass through the inner lumen of the delivery catheter and into the expandable member, wherein, when the light conducting fiber is in the expandable member, the light conducting fiber is able to disperse the light energy to initiate hardening of the at least one light sensitive liquid within the expandable member, forming a photodynamic implant of the present disclosure. In an embodiment, the expandable member is sufficiently designed to be contained within a head of a bone. In an embodiment, the expandable member is sufficiently designed such that a head section of the expandable member is within a head of a bone and a shaft section of the expandable member extends for a length into the shaft of the bone.

In an embodiment, a photodynamic implant of the present disclosure acts as a mandrel or form over which fragments of a head of a bone can be arranged to a substantially original position. In an embodiment, a photodynamic implant acts as a filler to return a head of a bone substantially to its original, anatomical shape prior to fracture or breaking In an embodiment, a photodynamic implant of the present disclosure is used for reattaching bone fragments of a head of a bone separated from the bone. In an embodiment, a photodynamic implant of the present disclosure is used for fixating a head of a bone separated from the bone. In an embodiment, a photodynamic implant of the present disclosure is used to re-align fragments of a broken bone to promote fracture restructure and stabilization. In an embodiment, a photodynamic implant of the present disclosure provides support and stability to a fractured or weakened bone during the natural healing process of the bone. In an embodiment, a photodynamic implant of the present disclosure is used to provide added strength to a weakened bone.

In an embodiment, a photodynamic implant of the present disclosure is configured to engage with another implant, including, but not limited to, a metal screw, rod, pin or nail. In an embodiment, a photodynamic implant of the present disclosure provides means to secure, bolt and pull the fractured bone segments back together into position. In an embodiment, a photodynamic implant of the present disclosure is used to fill a space within a fractured bone to return the fractured bone to its anatomical shape and is engaged to another implant that provides strength and stability to the shape. In an embodiment, a photodynamic implant of the present disclosure is configured to receive bone screws such that compressive force is exerted on bone fragments supported by the photodynamic implant.

In an embodiment, a photodynamic implant of the present disclosure is configured to fill interstitial space between a bone fixation implant and cortical bone to distribute load more evenly across the bone interface. That is, a photodynamic implant of the present disclosure acts as a filler between a bone fixation implant and a cortical bone interface so that load is not transferred through focal contact points between the bone fixation device and the cortical bone, but rather the load is distributed throughout a conformal contact in the bone.

A device for restructuring or stabilizing a fractured or weakened head of a bone is provided. The device includes: a delivery catheter having an elongated shaft with a proximal end, a distal end, and a longitudinal axis therebetween, an inner void for passing at least one light sensitive liquid, and an inner lumen; an expandable member releasably engaging the distal end of the delivery catheter; and a light conducting fiber sized to pass through the inner lumen of the delivery catheter and into the expandable member. The expandable member is capable of moving from a deflated state to an inflated state when the at least one light sensitive liquid is passed to the expandable member. The expandable member is sufficiently designed to be at least partially placed into a space within a head of a bone. When the light conducting fiber is in the expandable member, the light conducting fiber is able to disperse the light energy to initiate hardening of the at least one light sensitive liquid within the expandable member to form a photodynamic implant In an embodiment, the expandable member has a pear shape, bulb shape, dome shape, rounded shape, or elongated shape. In an embodiment, the expandable member has a tapered elongated shape. In an embodiment, the expandable member has a retrograde shape or an antegrade shape. In an embodiment, the expandable member has a proximal end and a distal end, and the diameter of the proximal end of the expandable member is larger than the diameter of the distal end of the expandable member. In an embodiment, the expandable member has a proximal end and a distal end, and the diameter of the distal end of the expandable member is larger than the diameter of the proximal end of the expandable member. In an embodiment, the expandable member is sufficiently designed to be contained within a head of a bone. In an embodiment, the expandable member includes a head section and a shaft section, and the expandable member is sufficiently designed such that the head section can be placed within a head of a bone and the shaft section can extend for a length into a shaft of the bone.

In an embodiment, the photodynamic implant is configured to engage with at least one bone fixation implant. In an embodiment, the at least one bone fixation implant is a screw, rod, pin, nail, or combination thereof. In an embodiment, the light conducting fiber includes a core and a cladding disposed on the core, and the cladding has at least one cut therein to expose the core and configured to alter the light exuded from the light conducting fiber.

In one aspect, a kit for repairing or stabilizing a fractured or weakened head of a bone includes: a light conducting fiber; at least one light sensitive liquid; a delivery catheter having an elongated shaft with a proximal end, a distal end, and a longitudinal axis therebetween, an inner void, and an inner lumen; and an expandable member releasably engaging the distal end of the delivery catheter. The expandable member is sufficiently designed to be at least partially placed into a space within a head of a bone. The delivery catheter has an inner void for passing the at least one light sensitive liquid into the expandable member, and an inner lumen for passing the light conducting fiber into the expandable member. In an embodiment, the kits includes a plurality of expandable members of different sizes or shapes. In an embodiment, the kit includes a light source.

In one aspect, a method for repairing or stabilizing a fractured or weakened head of a bone includes: placing an expandable member removably attached to a distal end of a delivery catheter at least partially into a space within a head of a bone; infusing a light sensitive liquid into the expandable member through an inner lumen of the delivery catheter; inserting a light conducting fiber into the expandable member through an inner void of the delivery catheter; and activating the light conducting fiber to cure the light sensitive liquid inside the expandable member to form a photodynamic implant inside the head of the bone. In an embodiment, the expandable member has a tapered elongated shape.

In an embodiment, the method includes disposing a head section of the expandable member within a head of a bone and extending a shaft section of the expandable member for a length into the shaft of the bone. In an embodiment, the method includes engaging the photodynamic implant with at least one bone fixation implant. In an embodiment, the at least one bone fixation implant is a screw, rod, pin, nail, or combination thereof. In an embodiment, the bone is a femur or a humerus.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 1B and FIG. 1C show schematic illustrations of embodiments of a bone implant device that includes a delivery catheter and an expandable member sufficiently shaped to fit within a space or a gap in a fractured bone.

FIG. 2A and FIG. 2B show close-up cross-sectional views of the region circled in FIG. 1A. FIG. 2A shows a cross-sectional view of a distal end of the delivery catheter and the expandable member prior to the device being infused with light-sensitive liquid. FIG. 2B shows a cross-sectional view of the distal end of the delivery catheter and the expandable member after the device has been infused with light-sensitive liquid and light energy from the light-conducting fiber is introduced into the delivery catheter and inner lumen of the expandable member to cure the light-sensitive liquid.

FIG. 2C and FIG. 2D show a close-up cross-sectional view of the regions circled in FIG. 1B and FIG. 1C, respectively. FIG. 2C and FIG. 2D show a cross-sectional view of a distal end of the delivery catheter and the expandable member and a light-conducting fiber in the delivery catheter and inner lumen of the expandable member.

Figure 1A:
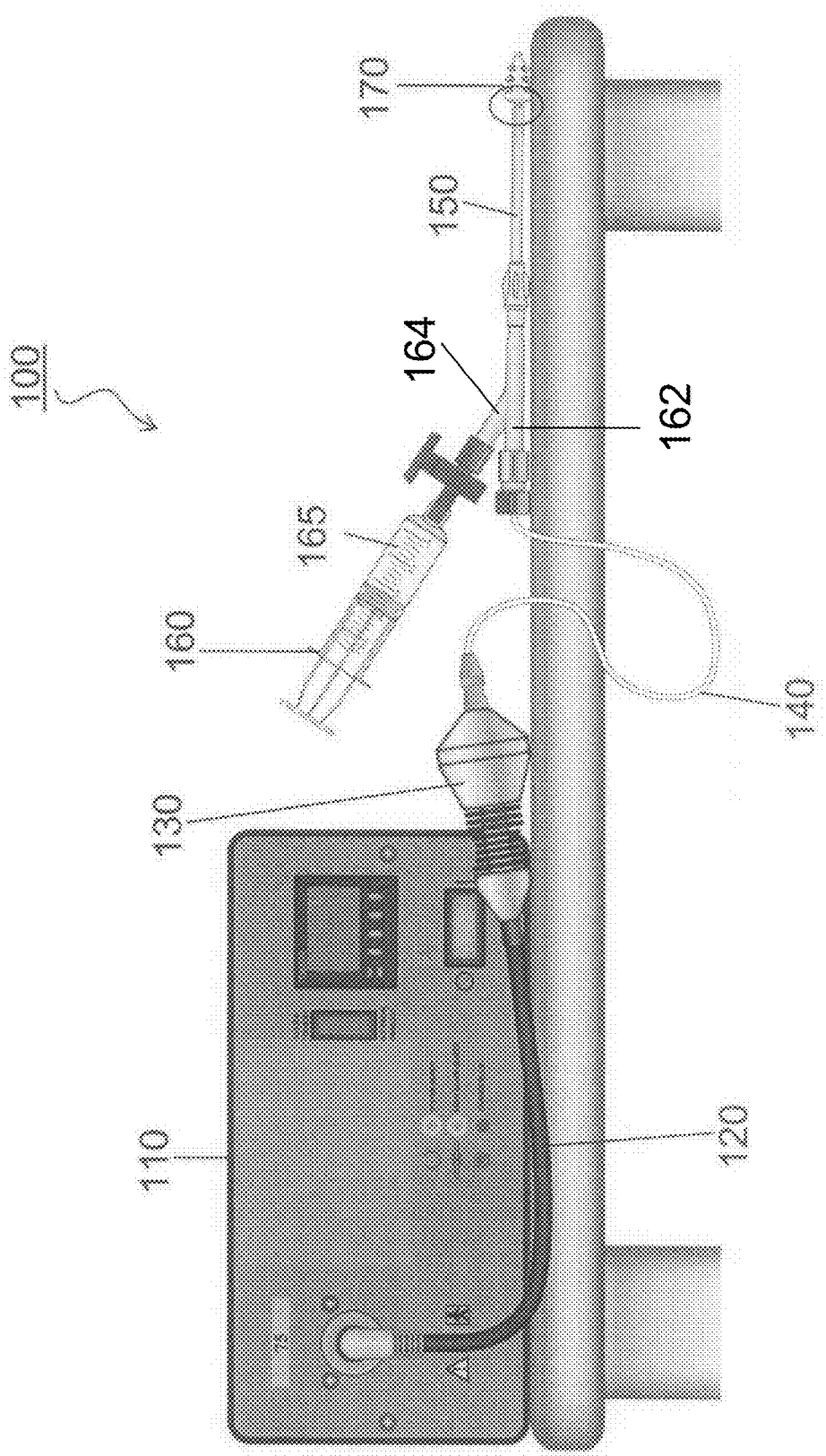
FIG. 1A shows a schematic illustration of an embodiment of a bone implant system of the present disclosure. The system includes a light source, a light pipe, an attachment system, a light-conducting fiber, a light-sensitive liquid, a delivery catheter and an expandable member sufficiently shaped to fit within a space or a gap in a fractured bone.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Devices and methods for bone restructure and stabilization are disclosed herein. In an embodiment, the present disclosure is directed to devices and methods for human treatment of bone fractures. In an embodiment, the present disclosure is directed to devices and methods for veterinary treatment of a fractured or a weakened bone. In an embodiment, devices and methods are provided for restructure, alignment and stabilization of a bone having a rounded head. The devices of the present disclosure are suitable to treat any fractured or weakened bone including, but not limited to, tibia, femur, fibula, humerus, ulna, radius, metatarsals, metacarpals, phalanx, phalanges, ribs, spine, vertebrae, clavicle, pelvis, wrist, mandible, and other bones. In an embodiment, a bone implant system of the present disclosure is used to treat a fractured or weakened proximal humerus. In an embodiment, a bone implant system of the present disclosure is used to treat a fractured or weakened femoral head.

As used herein, the terms "fracture" or "fractured bone" refer to a partial or complete break in the continuity of a bone. The fracture can occur, for example, from an outside force or from a controlled surgical cut (osteotomy). The presently disclosed embodiments can be used to treat any type of bone fracture, including, but not limited to, a displaced fracture, a non-displaced fracture, an open fracture, a closed fracture, a hairline fracture, a compound fracture, a simple fracture, a multi-fragment fracture, a comminuted fracture, an avulsion fracture, a buckle fracture, a compacted fracture, a stress fracture, a compression fracture, spiral fracture, butterfly fracture, other fractures as described by AO Foundation coding, multiple fractures in a bone, and other types of fractures.

As used herein, the term "weakened bone" refers to a bone with a propensity toward a fracture due to a decreased strength or stability due to a disease or trauma. Some bone diseases that weaken the bones include, but are not limited to, osteoporosis, achondroplasia, bone cancer, fibrodysplasia ossificans progressiva, fibrous dysplasia, legg calve perthes disease, myeloma, osteogenesis imperfecta, osteomyelitis, osteopenia, osteoporosis, Paget's disease, and scoliosis. Weakened bones are more susceptible to fracture, and treatment to prevent bone fractures may be desirable.

As used herein, the term "photodynamic implant" refers to an expandable member of the present disclosure that is infused with a photodynamic (light curable) material and exposed to an appropriate frequency of light and intensity to cure the material inside the expandable member and form a rigid structure.

As used herein, the terms "bone restructuring" or "restructure" refer to positioning a fractured bone back to a substantially normal, anatomically-correct position (separation of the bone fragments) and/or shape as well as supporting or stabilizing a weakened bone. In an embodiment, a photodynamic implant of the present disclosure provides a template, mandrel or form for restructuring a fractured or weakened bone. That is, a photodynamic implant of the present disclosure acts as a template, mandrel or form over which the fragments of a fractured bone can be arranged to a substantially original position and/or to which the fragments can be secured in a substantially original position. In an embodiment, a photodynamic implant of the present disclosure acts as a template, mandrel or form to return a broken bone to its a substantially normal, anatomically-correct shape. In an embodiment, a photodynamic implant of the present disclosure acts as a template, mandrel or form to support or stabilize a weakened bone in its a substantially normal, anatomically-correct shape. In an embodiment, a photodynamic implant of the present disclosure is used to restructure a fractured bone by aiding in attachment of a broken-off portion of a bone to the intact portion of the bone. In an embodiment, a photodynamic implant of the present disclosure is used to add strength to a weakened bone to prevent further weakening or a potential fracture.

In an embodiment, the present device is used in a minimally invasive surgical procedure. The device can enter a minimally invasive incision or access hole of any suitable size. For example, the access hole is about 5 mm to about 6 mm in diameter or any other suitable dimensions. In an embodiment, an expanding reamer or burr is used to pass through the small access hole. When inserted, the reamer is opened up to create a larger hole in the bone.

FIG. 1A shows a schematic illustration of an embodiment of a bone implant system 100. As shown in FIG. 1A, the system 100 includes a light source 110, a light pipe 120, an attachment system 130 and a light-conducting fiber 140. The attachment system 130 communicates light energy from the light source 110 to the light-conducting fiber 140. In an embodiment, the light source 110 emits frequency that corresponds to a band in the vicinity of 390 nm to 770 nm, the visible spectrum. In an embodiment, the light source 110 emits frequency that corresponds to a band in the vicinity of 410 nm to 500 nm. In an embodiment, the light source 110 emits frequency that corresponds to a band in the vicinity of 430 nm to 450 nm. The system 100 further includes a flexible delivery catheter 150 having a proximal end that includes at least two ports and a distal end terminating in an expandable member 170. The expandable member 170 of FIG. 1A has a bulbous shape, but may have any other suitable shape.

FIG. 1B and FIG. 1C show schematic illustrations of embodiments of a bone implant device 200. The devices 200 include a delivery catheter 150 and an expandable member 170 sufficiently shaped to fit within a space or a gap in a fractured bone. The expandable members 170 of FIG. 1B and FIG. 1C have a tapered elongated shape to fill the space or gap in certain fractured or weakened bones to be repaired or stabilized. In an embodiment, the expandable member 170 has an antegrade shape as shown in FIG. 1B. In an embodiment, the expandable member 170 has a retrograde shape as shown in FIG. 1C. In FIG. 1B, the expandable member 170 has a larger diameter at its distal end than the proximal end. In FIG. 1C, the expandable member 170 has a larger diameter at its proximal end than the distal end.

In an embodiment, the maximum diameter of the larger portion of the expandable member 170 is at least 1.5 times larger than the maximum diameter of the smaller portion of the expandable member 170. In an embodiment, the maximum diameter of the larger portion of the expandable member 170 is at least two times larger than the maximum diameter of the smaller portion of the expandable member 170.

In an embodiment, shown in FIG. 1B, the maximum diameter of the proximal portion of the expandable member 170 is at least 1.5 times the maximum diameter of the distal portion of the expandable member 170. In an embodiment, the maximum diameter of the proximal portion of the expandable member 170 is at least two times the maximum diameter of the distal portion of the expandable member 170.

In an embodiment, shown in FIG. 1C, the maximum diameter of the distal portion of the expandable member 170 is at least 1.5 times the maximum diameter of the proximal portion of the expandable member 170. In an embodiment, the maximum diameter of the distal portion of the expandable member 170 is at least two times the maximum diameter of the proximal portion of the expandable member 170.

The various shapes of the expandable member 170 allow for different approaches during minimally invasive surgical treatment of weakened or fractured bones. For example, an expandable member 170 having a retrograde or antegrade shape can be used for repair of a weakened or fractured proximal humerus. The antegrade shape allows for placement of the portion of the expandable member 170 with the largest diameter at the bone location most in need of repair or stabilization, including above and below the surgical neck area. For example, in the case of a proximal humerus, the antegrade shape allows for an incision and entry point into the humeral head through or just lateral to the rotator cuff. The geometry of the retrograde shape is opposite to the antegrade shape. With the retrograde shape, the portion of the expandable member 170 with the largest diameter is placed at the distal end of the catheter 150. The retrograde shaped expandable member 170 having the largest diameter can be placed at the bone location most in need of repair or stabilization, including above and below the surgical neck area. When repairing a proximal humerus, the retrograde shape allows for distal placement through an incision and bone entry point at (1) the medial or lateral epicondyles or (2) between these condyles at the roof of the olecranon fossa. In an embodiment, a device includes a retrograde shape expandable member 170 and has a longer catheter 150 (for example, about 3-4 inches longer) due to the increased distance from the bone access hole to the surgical neck.

In an embodiment, the expandable member 170 is sufficiently shaped to fit within a space or a gap in a fractured or weakened bone. One or more radiopaque markers, bands or beads may be placed at various locations along the expandable member 170 and/or the flexible delivery catheter 150 so that components of the system 100 may be viewed using fluoroscopy.

In the embodiments shown in FIG. 1A, FIG. 1B, and FIG. 1C, the proximal end of the delivery catheter 150 includes a first port 162 and a second port 164. The first port 162 can accept, for example, the light-conducting fiber 140. The second port 164 can accept, for example, a syringe 160 housing a light-sensitive liquid 165. In an embodiment, the syringe 160 maintains a low pressure during the infusion and aspiration of the light-sensitive liquid 165. In an embodiment, the syringe 160 maintains a low pressure of about 10 atmospheres or less during the infusion and aspiration of the light-sensitive liquid 165. In an embodiment, the syringe 160 maintains a low pressure of less than about 5 atmospheres during the infusion and aspiration of the light-sensitive liquid 165. In an embodiment, the syringe 160 maintains a low pressure of about 4 atmospheres or less during the infusion and aspiration of the light-sensitive liquid 165. In an embodiment, the light-sensitive liquid 165 is a photodynamic (light-curable) monomer. In an embodiment, the photodynamic (light-curable) monomer is exposed to an appropriate frequency of light and intensity to cure the monomer inside the expandable member 170 and form a rigid structure. In an embodiment, the photodynamic (light-curable) monomer 165 is exposed to electromagnetic spectrum that is visible (frequency that corresponds to a band in the vicinity of 390 nm to 770 nm). In an embodiment, the photodynamic (light-curable) monomer 165 is radiolucent, which permit x-rays to pass through the photodynamic (light-curable) monomer 165. In an embodiment, the delivery catheter 150 has one or more ports.

FIG. 2A and FIG. 2B show close-up cross-sectional views of the region circled in FIG. 1. FIG. 2A shows a cross-sectional view of a distal end of the delivery catheter 150 and the expandable member 170 prior to the device being infused with light-sensitive liquid. FIG. 2B shows a cross-sectional view of the distal end of the delivery catheter 150 and the expandable member 170 after the device has been infused with light-sensitive liquid and light energy from the light-conducting fiber is introduced into the delivery catheter 150 and inner lumen of the expandable member 170 to cure the light-sensitive liquid.

As illustrated in FIG. 2A and FIG. 2B, the flexible delivery catheter 150 includes an inner void 152 for passage of the light-sensitive liquid 165, and an inner lumen 154 for passage of the light-conducting fiber 140. In the embodiment illustrated in FIG. 2A and FIG. 2B, the inner lumen 154 and the inner void 152 are concentric to one another. The light-sensitive liquid 165 has a low viscosity or low resistance to flow, to facilitate the delivery of the light-sensitive liquid 165 through the inner void 152. In an embodiment, the light-sensitive liquid 165 has a viscosity of about 1000 cP or less. In an embodiment, the light-sensitive liquid 165 has a viscosity ranging from about 650 cP to about 450 cP. The expandable member 170 may be inflated, trial fit and adjusted as many times as a user wants with the light-sensitive liquid 165, up until the light source 110 is activated, when the polymerization process is initiated. Because the light-sensitive liquid 165 has a liquid consistency and is viscous, the light-sensitive liquid 165 may be delivered using low pressure delivery and high pressure delivery is not required, but may be used.

FIG. 2C and FIG. 2D show a close-up cross-sectional view of the region circled in FIG. 1B and FIG. 1C, respectively. FIG. 2C and FIG. 2D show cross-sectional views of a distal end of the delivery catheter 150 and the expandable member 170 and a light-conducting fiber 140 in the delivery catheter 150 and inner lumen of the expandable member 170. The device also has a separation area 172 at the junction of the delivery catheter 150 and the expandable member 170 where the delivery catheter 150 may be separated from the expandable member 170.

In an embodiment, a contrast material may be added to the light-sensitive liquid 165 without significantly increasing the viscosity. Contrast materials include, but are not limited to, barium sulfate, tantalum, or other contrast materials known in the art. The light-sensitive liquid 165 can be introduced into the proximal end of the flexible delivery catheter 150 and passes within the inner void 152 of the flexible delivery catheter 150 up into an inner cavity 172 of the expandable member 170 to change a thickness of the expandable member 170 without changing a width or depth of the expandable member 170. In an embodiment, the light-sensitive liquid 165 is delivered under low pressure via the syringe 160 attached to the second port 164. The light-sensitive liquid 165 can be aspirated and reinfused as necessary, allowing for thickness adjustments to the expandable member 170 prior to activating the light source 110 and converting the liquid monomer 165 into a hard polymer.

In an embodiment, the light-sensitive liquid may be provided as a unit dose. As used herein, the term "unit dose" is intended to mean an effective amount of light sensitive liquid adequate for a single session or treatment. By way of a non-limiting example, a unit dose of a light sensitive liquid of the present disclosure for expanding the expandable member 170 may be defined as enough light-sensitive liquid to expand the expandable member 170 to a desired shape and size. In an embodiment, the expandable member 170 is sufficiently shaped and sized to fit within a space or a gap in a fractured bone. The desired shape and size of the expandable member 170 may vary somewhat from patient to patient. Thus, a user using a unit dose may have excess light-sensitive liquid left over after the procedure. It is desirable to provide sufficient amount of light-sensitive liquid to accommodate even the above-average patient. In an embodiment, a unit dose of a light-sensitive liquid of the present disclosure is contained within a container.

In an embodiment, a unit dose of a light-sensitive liquid of the present disclosure is contained in an ampoule. In an embodiment, the light-sensitive liquid can be delivered under low pressure via a standard syringe attached to the second port 164. In an embodiment, the light-sensitive liquid can be delivered without use of a pump.

As illustrated in FIG. 1A in conjunction with FIG. 2B, the light-conducting fiber 140 can be introduced into the proximal end of the flexible delivery catheter 150 via the first port 162 and passes within the inner lumen 154 of the flexible delivery catheter 150 up into the expandable member 170. The light-conducting fiber 140 is used in accordance to communicate energy in the form of light from the light source 110 to a remote location. The light-sensitive liquid 165 remains a liquid monomer until activated by the light-conducting fiber 140 (cures on demand). Radiant energy from the light source 110 is absorbed and converted to chemical energy to polymerize the monomer. The light-sensitive liquid 165, once exposed to the correct frequency light and intensity, is converted into a hard polymer, resulting in a rigid structure or photodynamic implant of the present disclosure. The monomer may cure in any amount of time. In an embodiment, the monomer in the light sensitive liquid 165 cures in about five seconds to about five minutes. This cure affixes the expandable member 170 in an expanded shape to form a photodynamic implant of the present disclosure. A cure may refer to any chemical, physical, and/or mechanical transformation that allows a composition to progress from a form (e.g., flowable form) that allows it to be delivered through the inner void 162 in the flexible delivery catheter 150, into a more permanent (e.g., cured) form for final use in vivo. For example, "curable" may refer to uncured light-sensitive liquid 165, having the potential to be cured in vivo (as by catalysis or the application of a suitable energy source), as well as to a light-sensitive liquid 165 in the process of curing (e.g., a composition formed at the time of delivery by the concurrent mixing of a plurality of composition components).

Light-conducting fibers use a construction of concentric layers for optical and mechanical advantages. Suitable light-conducting fiber 140 can be made from any material, including, but not limited to, glass, silicon, silica glass, quartz, sapphire, plastic, combinations of materials, or any other material, and may have any diameter. In an embodiment, the light-conducting fiber may be made from a polymethyl methacrylate core with a transparent polymer cladding. The light-conducting fiber 140 has any suitable diameter. In an embodiment, the light-conducting fiber has a diameter between approximately 0.75 mm and approximately 2.0 mm. In some embodiments, the light-conducting fiber can have a diameter of about 0.75 mm, about 1 mm, about 1.5 mm, about 2 mm, less than about 0.75 mm or greater than about 2 mm.

In an embodiment, one or more light conducting fibers 140 are used. Using more than one light conducting fibers 140 may reduce the cure time of the light-sensitive liquid, particularly when used with larger expandable members 170. In an embodiment, a plurality of light conducting fibers 140 are positioned side-by-side or in parallel in the expandable member 170. In an embodiment, a plurality of light conducting fibers 140 are positioned serially with ends of adjacent light conducting fibers 140 aligned or abutting on another in an end to end fashion. For example, one light conducting fiber may be positioned in the distal portion of the expandable member and another light conducting fiber may be positioned in the proximal portion of the expandable member 170. In an embodiment, a plurality of light conducting fibers are positioned in a combination of parallel and serial positions, such as partially overlapping or any other suitable configuration. In an embodiment, a plurality of light conducting fibers can be attached to a single light source with a splitter, or can be attached to a plurality of light sources.

In an embodiment, when a plurality of light conducting fibers 140 are used, an inner lumen of a delivery catheter 150 has a larger inner diameter. In an embodiment, an inner lumen of the delivery catheter 150 has an inner diameter of about 1.8 mm. In an embodiment, an inner lumen of the delivery catheter is sized to contain a plurality of light conducting fibers 140. In an embodiment, a delivery catheter sized to contain a plurality of light conducting fibers 140 has an inner diameter of about 2.3 mm to about 3.0 mm.

In an embodiment, the light-conducting fiber 140 is made from a polymethyl methacrylate core with a transparent polymer cladding. It should be appreciated that the above-described characteristics and properties of the light-conducting fibers 140 are exemplary and not all embodiments of the present disclosure are intended to be limited in these respects. Light energy from a visible emitting light source can be transmitted by the light-conducting fiber 140. In an embodiment, visible light having a wavelength spectrum of between about 380 nm to about 780 nm, between about 400 nm to about 600 nm, between about 420 nm to about 500 nm, between about 430 nm to about 440 nm or any other suitable wavelengths, is used to cure the light-sensitive liquid.

The most basic function of a fiber is to guide light, i.e., to keep light concentrated over longer propagation distances despite the natural tendency of light beams to diverge, and possibly even under conditions of strong bending. In the simple case of a step-index fiber, this guidance is achieved by creating a region with increased refractive index around the fiber axis, called the fiber core, which is surrounded by the cladding. The cladding may be protected with a polymer coating. Light is kept in the "core" of the light-conducting fiber by total internal reflection. Cladding keeps light traveling down the length of the fiber to a destination. In some instances, it is desirable to conduct electromagnetic waves along a single guide and extract light along a given length of the guide's distal end rather than only at the guide's terminating face.

In some embodiments of the present disclosure, at least a portion of a length of a light-conducting fiber is modified, e.g., by removing the cladding, in order to alter the profile of light exuded from the light-conducting fiber. The term "profile of light" refers to, without limitation, direction, propagation, amount, intensity, angle of incidence, uniformity, distribution of light and combinations thereof. In an embodiment, the light-conducting fiber emits light radially in a uniform manner, such as, for example, with uniform intensity, along a length of the light-conducting fiber in addition to or instead of emitting light from its terminal end/tip. To that end, all or part of the cladding along the length of the light-conducting fiber may be removed. It should be noted that the term "removing cladding" includes taking away the cladding entirely to expose the light-conducting fiber as well as reducing the thickness of the cladding. In addition, the term "removing cladding" includes forming an opening, such as a cut, a notch, or a hole, through the cladding. In an embodiment, removing all or part of the cladding may alter the propagation of light along the light-conducting fiber. In another embodiment, removing all or part of the cladding may alter the direction and angle of incidence of light exuded from the light-conducting fiber.

FIG. 1B, FIG. 1C, FIG. 2C, and FIG. 2D show an example of a light-conducting fiber having a cut 141 in the cladding along the length of the light-conducting fiber to modify light exuding from the light-conducting fiber.

Figure 3A:
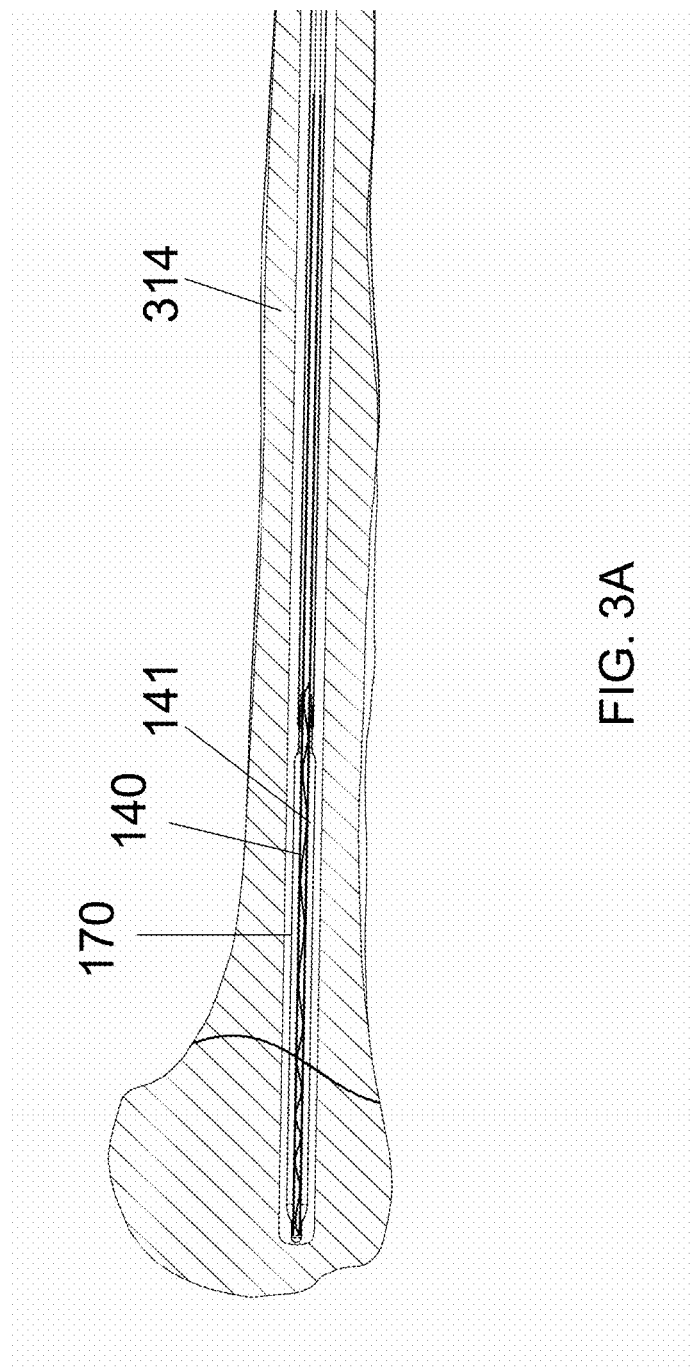
FIG. 3A illustrates a cross-section view of an embodiment of a device in a cavity of a bone prior to inflation of the expandable member.

FIG. 3A illustrates an embodiment of a device in a cavity of a bone 314 prior to inflation of the expandable member 170. In an embodiment, as shown in FIG. 3A, the cladding of the light-conducting fiber 140 is removed by making a cut 141 in the cladding to expose the core of the light-conducting fiber 140. In an embodiment, the cut 141 is a continuous cut extending for the entire length of the modified section. In an embodiment, the cut 141 includes multiple discontinuous cuts. In an embodiment, the cladding is removed in such a way that a similar amount of light is exuded along the modified section of the light-conducting fiber. In another embodiment, the cladding is removed in such a way that a different amount of light is exuded along the modified section of the light-conducting fiber. In another embodiment, the cladding is removed in such a way that the amount of light exuded along the modified section of the light-conducting fiber decreases from the distal end of the modified section of the light-conducting fiber toward the proximal end thereof. In an embodiment, to alter the profile of the light exuded from the modified section, the cuts in the cladding are located along the length of the fiber in a spiral, as shown in FIG. 3A. In an embodiment, the pitch or spacing between the cuts is varied along the length of the modified section of the light-conducting fiber. In an embodiment, the spacing between the cuts increases from the proximal end of the modified section of the light-conducting fiber 140 to the distal end thereof such that the amount of light exuded from the modified section of the light-conducting fiber 140 progressively increases toward the distal end of the modified section of the light-conducting fiber 140.

Figure 3B:
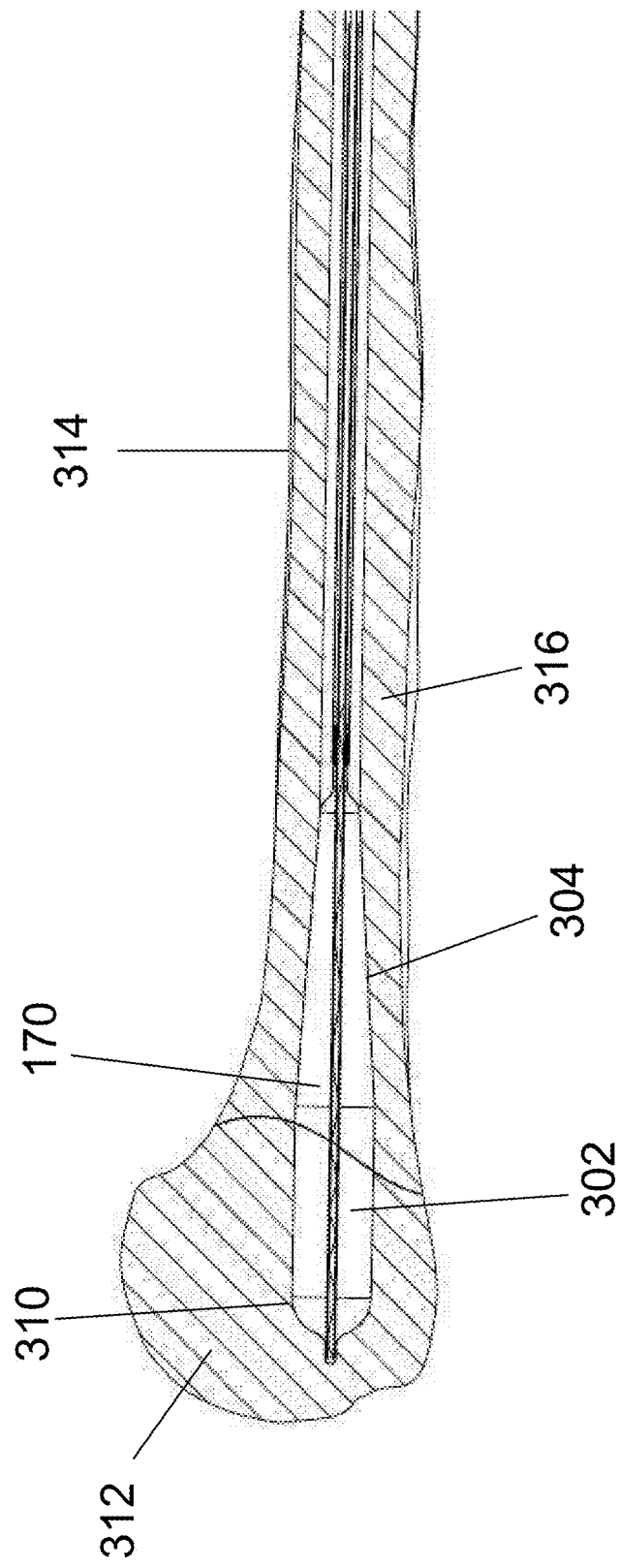
FIG. 3B illustrates a cross-section view of an embodiment of a device in a cavity of a bone after inflation of the expandable member.

FIG. 3B is a schematic illustration showing an embodiment of an expandable member 170 in the expanded state in a cavity of a bone 314. As shown in FIG. 3B, the expandable member 170 is sufficiently designed for placement into a space 310 within a head 312 of a bone 314, including, but not limited to, a humerus or a femur. In an embodiment, the expandable member 170 approximates the shape of the head 312 and is configured to be placed within the head 312. In an embodiment, the expandable member 170 is provided with shape and size to enable reconstruction of the head 312. In an embodiment, the expandable member 170 can be pear-shaped, light-bulb shaped, or elongated. FIG. 3B shows an example of an expandable member 170 that is elongated.

In an embodiment, the expandable member 170 includes a head section 302, i.e. an enlarged upper section, that merges into a shaft section 304, i.e. a tapered or frusto-conical lower section. In an embodiment, the head section 302 tapers gradually to form the shaft section 304, which can extend from the head 312 into a shaft 316 of the bone 314. In an embodiment, the expandable member 170, including both the head section 302 and the shaft section 304, is configured to be contained in the space 310 within the head 312. In an embodiment, the shaft section 304 of the expandable member 170 extends for any desired distance into the shaft 316 of the bone 314. In an embodiment, the shaft section 304 of the expandable member 170 extends into the shaft 316 of the bone 314 for about 50 mm to about 300 mm.

Figure 4A:
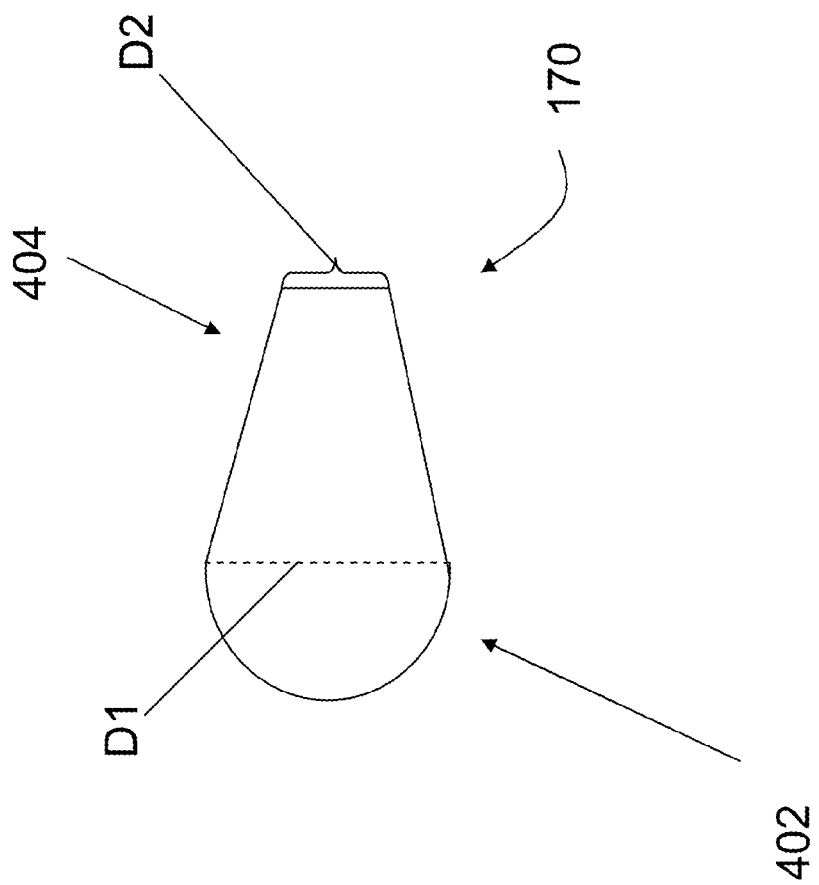
FIG. 4A and FIG. 4B show schematic illustrations of embodiments of an expandable member.
Figure 4B:
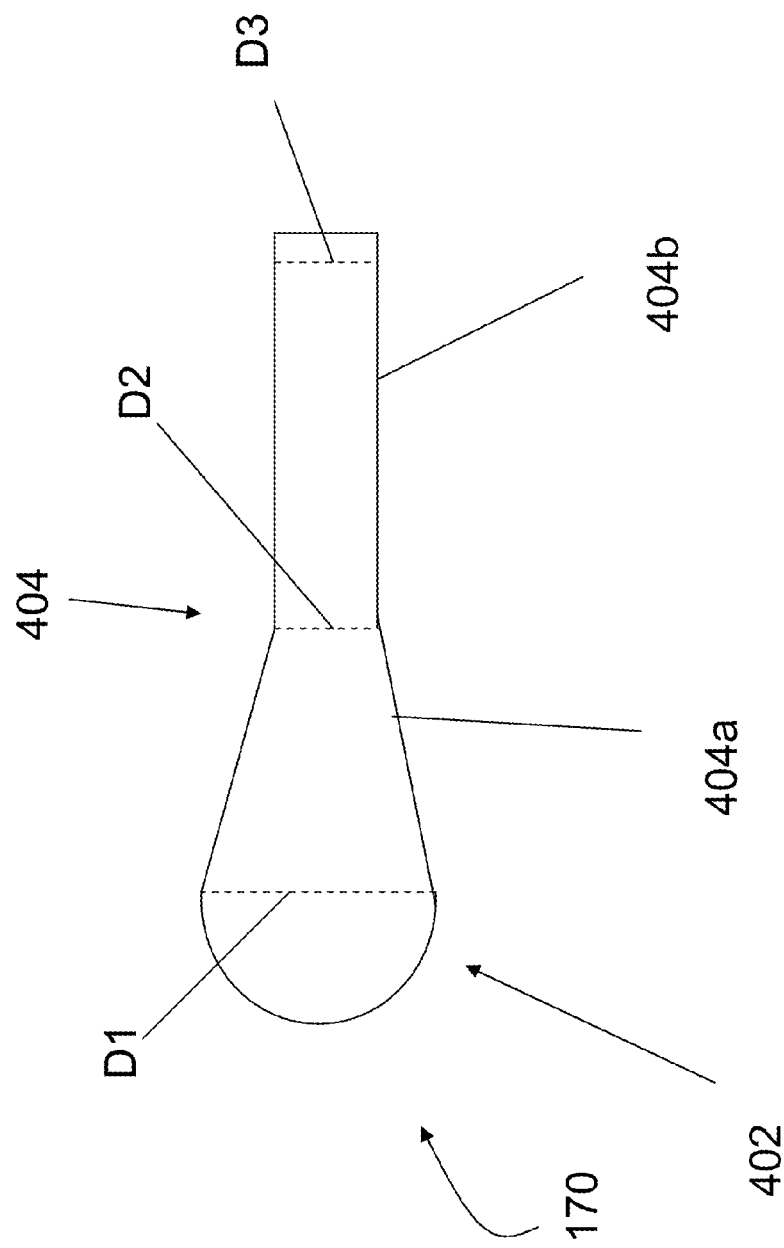

FIG. 4A and FIG. 4B show schematic illustrations of embodiments of an expandable member 170. As shown in FIG. 4A, in an embodiment, the head section 402 is dome-shaped or rounded. The bulbous shape of the head 412 has a diameter D1 that is larger than the diameter D2 of the shaft section of the implant. In an embodiment, the diameter D1 of the head section 402 is at least double the diameter D2 of the shaft section 404. In an embodiment, the diameter D1 of the head section 402 is at least triple the diameter D2 of the shaft section 404. In various embodiments, the diameter D1 of the head section 402 is 2.5 times, 3.5 times, 4 times, 5 times, 10 times or more larger than the diameter D2 of the shaft section 404. In an embodiment, the head section may be about 20 to 35 mm in diameter at a distal part of the implant (for example, anatomically the proximal head of the humerus), tapering in the frusto-conical shaft section to 10 to 15 mm. In an embodiment, the shaft section 404 is generally triangular or tapered. In an embodiment, the shaft section 404 is generally frusto-conical. The expandable member 170, including the head section 402 and the shaft section 404, may be formed as a single piece, or, alternatively, these sections can be mated to one another via a screwed-in section, a through hole, or any other suitable mechanism.

As shown in FIG. 4B, in an embodiment, the shaft section 404 of the expandable member 170 can include a transition portion 404a extending from the head section 402 and an extension portion 404b extending distally from the head 412 from the tapered portion 404a into the intramedullary cavity. The transition portion 404a can be tapered or frusto-conical and the extension portion can be either uniform or tapered. In an embodiment, the diameter D2 of the transition portion 404 is substantially the same as the diameter D3 of the extension portion 404b. In an embodiment, the diameter D2 of the transition portion 404a is 1.5 times, 2 times, 3 times or more larger than the diameter D3 of the extension portion 404b. In an embodiment, the diameter D1 of the head section 402 is at least double the diameter D3 of the extension portion 404b of the shaft section 404. In an embodiment, the diameter D1 of the head section 402 is at least triple the diameter D3 of the extension portion 404b of the shaft section 404. In various embodiments, the diameter D1 of the head section 402 is 2.5 times, 3.5 times, 4 times, 5 times, 10 times or more larger than the diameter D3 of the extension portion 404b of the shaft section 404.

In an embodiment, the expandable member 170 can be round or oval for placement into the space 410 within the head 412 of the bone 414. It should be noted that the expandable member 170 may have any other shape suitable for placement into a head of a bone. Suitable additional shapes include, but are not limited to, a sphere, ovoid sphere, tapered cone, three-dimensional wedge whereby one axis is significantly wider than the other, with both tapering from a larger dimension to a smaller dimension, and similar. As discussed above, the expandable member 170 can be a tapered elongated shape such as an antegrade shape or a retrograde shape, as shown in FIG. 1B and FIG. 1C, respectively.

In an embodiment, the external surface of the expandable member 170 is resilient and puncture resistant. In an embodiment, the expandable member 170 is manufactured from a non-compliant (non-stretch/non-expansion) conformable material including, but not limited to, urethane, polyethylene terephthalate (PET), nylon elastomer and other similar polymers. In an embodiment, the expandable member 170 is manufactured from a polyethylene terephthalate (PET). In an embodiment, the expandable member 170 is manufactured from a radiolucent material, which permit x-rays to pass through the expandable member 170. In an embodiment, the expandable member 170 is manufactured from a radiolucent polyethylene terephthalate (PET). In an embodiment, the expandable member 170 is manufactured from a conformable compliant material that is limited in dimensional change by embedded fibers. In an embodiment, at least a portion of the external surface 174 of the expandable member 170 is substantially even and smooth. In an embodiment, at least a portion of the external surface of the expandable member 170 includes at least one textured element such as a bump, a ridge, a rib, an indentation or any other shape. In an embodiment, at least a portion of the external surface of the expandable member 170 protrudes out to form a textured element. In an embodiment, at least a portion of the external surface of the expandable member 170 invaginates to form a textured element. In an embodiment, the textured element increases the friction and improves the grip and stability of the expandable member 170 after the expandable member 170 is inserted into the fracture location. In an embodiment, the textured element results in increased interdigitation of bone-device interface as compared to an expandable member without textured elements. In an embodiment, the textured element can be convex in shape. In an embodiment, the textured element can be concave in shape. In an embodiment, the textured element can be circumferential around the width of the expandable member 170, either completely or partially.

In general, bone graft or bone graft substitute can be used in conjunction with an expandable member 170 of the present disclosure. In an embodiment, the bone graft is an allogeneic bone graft. In an embodiment, the bone graft is an autologous bone graft. In an embodiment, the bone graft substitute is a hydroxyapatite bone substitute. In an embodiment, a bone graft or bone graft substitute is used to fill in any gaps that may exist, for example, between the external surface of the expandable member 170 and the surfaces of the bone fragments. In an embodiment, a bone graft or bone graft substitute is used to fill any gaps that may exist, for example, between the textured element of the expandable member 170 and the surfaces of the bone fragments.

In general, the expandable member 170 can include an external surface that may be coated with materials including, but not limited to, drugs (for example, antibiotics), proteins (for example, growth factors) or other natural or synthetic additives (for example, radiopaque or ultrasonically active materials). For example, after a minimally invasive surgical procedure an infection may develop in a patient, requiring the patient to undergo antibiotic treatment. An antibiotic drug may be added to the external surface of the expandable member 170 to prevent or combat a possible infection. Proteins, such as, for example, bone morphogenic protein or other growth factors have been shown to induce the formation of cartilage and bone. A growth factor may be added to the external surface of the expandable member 170 to help induce the formation of new bone. Due to the lack of thermal egress of the light-sensitive liquid 165 in the expandable member 170, the effectiveness and stability of the coating is maintained.

In an embodiment, the expandable member 170 does not have any valves. One benefit of not having valves is that the expandable member 170 may be expanded or reduced in size as many times as necessary to assist in the fracture reduction and placement. Another benefit of the expandable member 170 not having valves is the efficacy and safety of the system 100. Since there is no communication passage of light-sensitive liquid 165 to the body there cannot be any leakage of liquid 165 because all the liquid 165 is contained within the expandable member 170. In an embodiment, a permanent seal is created between the expandable member 170 and the delivery catheter 150 that is both hardened and affixed prior to the delivery catheter 150 being removed.

In an embodiment, abrasively treating the external surface of the expandable member 170 for example, by chemical etching or air propelled abrasive media, improves the connection and adhesion between the external surface of the expandable member 170 and a bone surface. The surfacing significantly increases the amount of surface area that comes in contact with the bone which can result in a stronger grip.

The expandable member 170 can be infused with light-sensitive liquid 165 and the light-sensitive liquid 165 can be cured to form a photodynamic implant the photodynamic implant may be separated from the delivery catheter 150. As shown in FIG. 3A and FIG. 3B, a separation area 142 is located at the junction between the distal end of the cured expandable member 170 (or photodynamic implant) and the delivery catheter 150 to facilitate the release of the photodynamic implant from the delivery catheter 150. The separation area 142 ensures that there are no leaks of reinforcing material from the elongated shaft of the delivery catheter and/or the photodynamic implant. The separation area seals the photodynamic implant and removes the elongated shaft of the delivery catheter by making a break at a known or predetermined site (e.g., a separation area). The separation area 142 may be various lengths and up to about an inch long. The separation area 142 may also include a stress concentrator, such as a notch, groove, channel or similar structure that concentrates stress in the separation area 142. The stress concentrator can also be an area of reduced radial cross section of cured light-sensitive liquid inside a contiguous cross sectional catheter to facilitate separating by the application of longitudinal force. The stress concentrator is designed to ensure that the photodynamic implant is separated from the delivery catheter 150 at the separation area 142. When tension is applied to the delivery catheter 150, the photodynamic implant separates from the shaft of the delivery catheter 150, substantially at the location of the stress concentrator. The tension creates a sufficient mechanical force to preferentially break the cured material and catheter composite and create a clean separation of the photodynamic implant/shaft interface. The photodynamic implant may be separated from the delivery catheter 150 by any other suitable means including, but not limited to, radial twisting, shear impact, and cross-sectional cutting.

In an embodiment, the shape of the photodynamic implant corresponds to the shape of the expandable member 170. In various embodiment, the photodynamic implant can be pear-shaped, oval, round, elongated, tapered, and the like. Modification of light-sensitive liquid 165 infusion allows a user to adjust the span or thickness of expandable member 170 to provide specific photodynamic implant size and shape to each subject. In that the expandable member 170 is formable and shapeable by the user prior to the photocuring of the light-sensitive liquid 165 in the expandable member 170, the photodynamic implant best mirrors the size and shape of the area into which the expandable member 170 is implanted. In an embodiment, the photodynamic implant is configured to be at least partially placed into a space within a head of a bone. In an embodiment, the photodynamic implant is configured to be contained within a head of a bone. In an embodiment, the photodynamic implant is configured such that a distal section of the implant extends for a length into the shaft of the bone.

In an embodiment, the photodynamic implant formed by infusing and curing the light sensitive liquid 165 into the expandable member 170 is used for restructuring, aligning and/or stabilizing a bone. In an embodiment, the expandable member 170 can be infused with an amount of light-sensitive liquid 165 such that the final cured photodynamic implant has the size and shape to substantially return a broken head of a bone to its anatomical shape. In an embodiment, the expandable member 170 can be infused with an amount of light-sensitive liquid 165 such that the photodynamic implant has the size and shape such that a head of a bone can be restructured to a substantially original size and shape around the final cured photodynamic implant. In an embodiment, the expandable member 170 can be infused with an amount of light-sensitive liquid 165 such that the photodynamic implant facilitates a reduction of a fractured bone. In an embodiment, the size and shape of the photodynamic implant 510 attempts to maximize the surface contact area with the surrounding bone, minimizing specific points of concentrated pressure. The photodynamic implant may be sufficiently designed to provide high compressive strength, thus minimizing deformation under dynamic loading conditions.

In an embodiment, the expandable member is positioned and inflated to a size sufficient to provide maximum fill of the cavity of the bone, such as an intramedullary canal, at the region of the fracture or weakened bone. The expandable member is inflated to any suitable size. In an embodiment, the expandable member is inflated up to about 20 mm in diameter.

Figure 5:
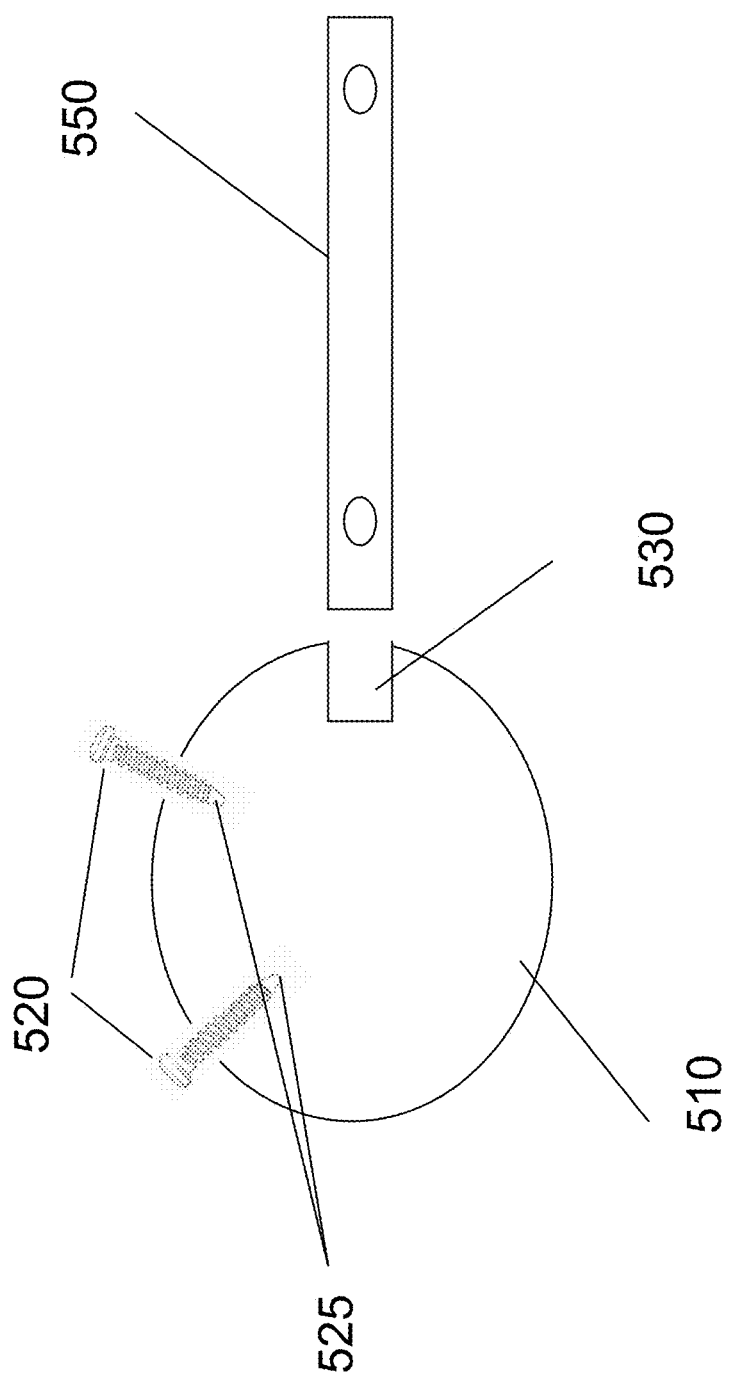
FIG. 5 is a schematic illustration of an embodiment of a photodynamic implant of the present disclosure.

FIG. 5 shows an embodiment of a photodynamic implant 510 that is designed to engage other bone fixation implants 520 including, but not limited to, bone screws, nails, pins and rods, among others. The bone fixation implants can engage the final cured photodynamic implant at any user-selected location along the photodynamic implant. For example, FIG. 5 illustrates a plurality of bone fixation implants 520 engaged with the photodynamic implant 510 at user-selected locations 525. In an embodiment, bone fragments can be secured in substantially original position by attaching the bone fragments to the final cured photodynamic implant with bone fixation implants. In an embodiment, the photodynamic implant 510 can be placed into a space within a head of a bone and one or more bone fixation implants can be inserted through the bone into the photodynamic implant 510 so as to fixate the head to the rest of the bone. In reference to FIG. 5, in an embodiment, the photodynamic implant 510 may include one or more receptacles 530 for receiving standard metallic implants. In an embodiment, the photodynamic implant 510 may include one or more receptacles 530 to engage an intramedullary nail or rod 550. The nail or rod 550 may be secured to the photodynamic implant 510 by any suitable means such as, for example, locking, snap-fit, friction fit or threading or similar.

In an embodiment, bone fixation implants including, but not limited to, screws and other suitable mechanisms are anchored into the cured expandable member or the photodynamic implant at the surgeons desired locations based on the fracture pathology and not the location of pre-determined locking holes. In an embodiment, the photodynamic implant are of a sufficiently large size to provide for a significant anchor and target above and below the fracture site for placement of multiple bone fixation implants including support cross-locking screws and any other suitable mechanisms.

Figure 6:
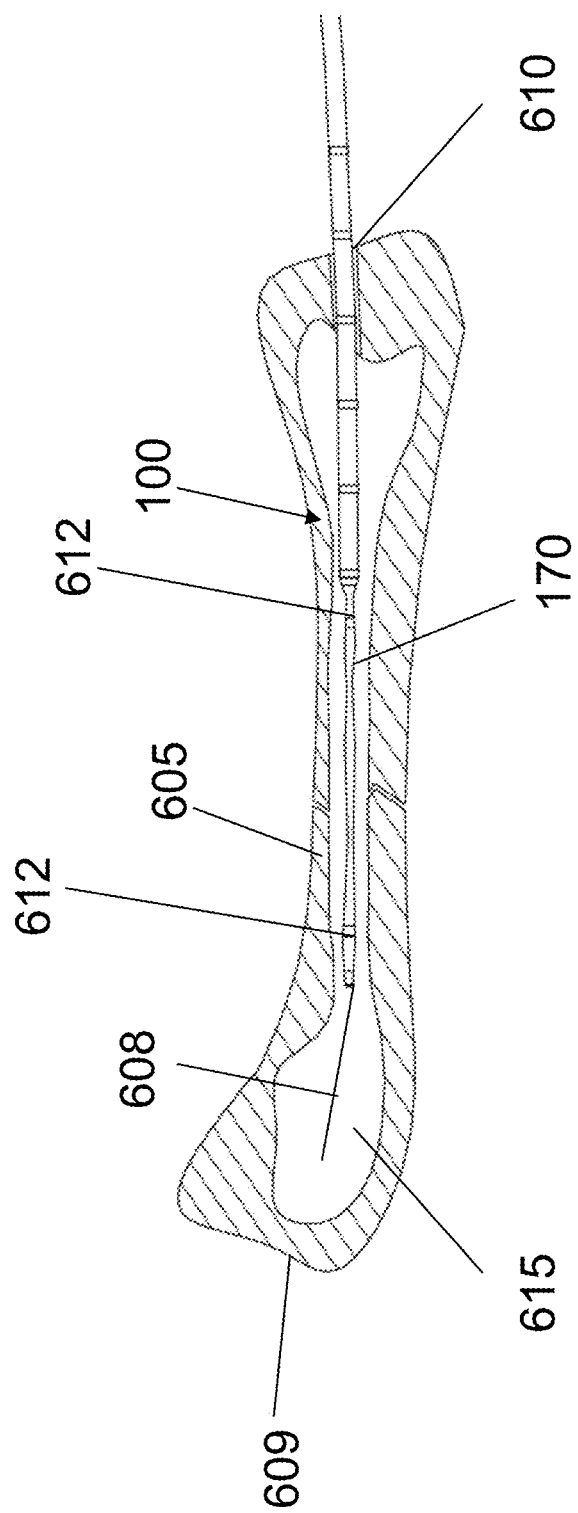
FIG. 6 illustrates a cross-sectional view of an embodiment of a device being inserted into a cavity of bone using the disclosed devices and methods.

FIG. 6 illustrates a device inserted into a cavity of bone using the present systems and methods. First, a minimally invasive incision (not shown) is made through the skin of the patient's body to expose a fractured bone. The incision may be made at the proximal end or the distal end of the fractured bone to expose the bone surface. Once the bone is exposed, it may be necessary to retract some muscles and tissues that may be in view of the bone. As shown in FIG. 6, an access hole 610 is formed in a bone 605 by drilling or other methods known in the art. The access hole extends through a hard compact outer layer of the bone into the relatively porous inner or cancellous tissue. For bones with marrow, the medullary material should be cleared from the medullary cavity prior to insertion of the system 100. Marrow is found mainly in the flat bones such as hip bone, breast bone, skull, ribs, vertebrae and shoulder blades, and in the cancellous material at the proximal ends of the bones like the femur and humerus. Once the medullary cavity is reached, the medullary material including air, blood, fluids, fat, marrow, tissue and bone debris should be removed to form a void. The void is defined as a hollowed out space, wherein a first position defines the most distal edge of the void with relation to the penetration point on the bone, and a second position defines the most proximal edge of the void with relation to the penetration site on the bone. The bone may be hollowed out sufficiently to have the medullary material of the medullary cavity up to the cortical bone removed. Any suitable method for removing the medullary material may be used. Suitable methods include, but are not limited to, those described in U.S. Pat. No. 4,294,251 entitled "Method of Suction Lavage," U.S. Pat. No. 5,554,111 entitled "Bone Cleaning and Drying system," U.S. Pat. No. 5,707,374 entitled "Apparatus for Preparing the Medullary Cavity," U.S. Pat. No. 6,478,751 entitled "Bone Marrow Aspiration Needle," and U.S. Pat. No. 6,358,252 entitled "Apparatus for Extracting Bone Marrow."

A guidewire 608 may be introduced into the bone 605 via the access hole 610 and advanced through the intramedullary cavity 615 of the bone 602 to a rounded head 609 of the bone 602. The expandable member 170 of the system 100 is then delivered over the guidewire 608 to be placed within the head 609 of the bone 602. The location of the expandable member 170 may be determined using at least one radiopaque marker 615 which is detectable from the outside or the inside of the bone 602. Once the expandable member 170 is in the correct position within the head 609, the light-sensitive liquid 165 is then infused into the expandable member 170 to cause the expandable member 170 to expand to a desired size and shape, as described above.

The light-sensitive liquid 165 can be cured inside the expandable member 170 using the light-conducting fiber 140, as shown in FIG. 3A. After the light-sensitive liquid 165 is hardened, the light-conducting fiber 140 can be removed from the system 100.

In an embodiment, an expandable member 170 is filled with the cured light-sensitive liquid 165 that is released from the delivery catheter 150 to form a photodynamic implant inside the head 609 of the bone 602, as shown in FIG. 3B. In an embodiment, a photodynamic implant of the present disclosure acts to return a broken bone substantially to its original, anatomical shape. In an embodiment, a photodynamic implant of the present disclosure acts as a mandrel over which fragments of a broken bone can be arranged to a substantially original position and to which the fragments can be attached by using bone fixation implants, including, but not limited to, bone screws, nails, pins and rods, among others. A bone fixation implants can be placed into a photodynamic implant of the present disclosure at any user-selected location on the photodynamic implant. In an embodiment, a photodynamic implant of the present disclosure is used for reattaching a bone fragment separated from a broken bone. In an embodiment, a photodynamic implant of the present disclosure is used to re-align fragments of a broken bone. In an embodiment, a photodynamic implant of the present disclosure provides support and stability to a fractured bone during the natural healing process of the bone. In an embodiment, a photodynamic implant of the present disclosure can be used to stabilize or add strength to a weakened bone.

In an embodiment, the photodynamic implant provides rotational stability by contouring to the cavity of the bone without the need for a significant number of locking screws or other bone fixation mechanisms, though such mechanisms may be used. Also, the expandable member is of a sufficient size to provide bending stability.

In an embodiment, a bone implant system 100 of the present disclosure is used to treat a fractured or weakened proximal humerus. In general, proximal humeral fractures are classified based on the number and type of major fragments. For example, a two-part fracture is typically a humeral neck fracture, separating the head of the humerus from the shaft of the humerus. More complicated fractures are three-part and four-part fractures. Three-part proximal humerus fractures can involve, for example, separation of greater tuberosity and humeral neck. Four-part fractures typically involve articular surface of the head and head splitting fractures. In an embodiment, a photodynamic implant of the present disclosure can be used to treat two-part, three-part, or four-part fractures of the proximal humerus. In an embodiment, a photodynamic implant of the present disclosure can be used to realign, restructure, stabilize or support the shaft of the humerus, greater tuberosity, humeral neck, articular surface of the head and head splitting fractures. In an embodiment, a photodynamic implant of the present disclosure can be used to stabilize a weakened humeral head, neck, shaft or other portions of humerus.

In an embodiment, access to the intramedullary cavity of a humerus can be obtained by either retrograde approach or an antegrade approach as described above. It should be noted that the orientation of the expandable member relative to the delivery catheter will change depending on the chosen approach. The expandable member 107 is placed within a space of cancellous bone near the top of the humeral head. Once the expandable portion 107 is in the correct position within the humerus, the expandable portion 107 is filled with the light-sensitive liquid 165, which is then cured resulting in the photodynamic implant 510. In an embodiment, the bone implant system 100 is used to treat a humeral neck fracture, separating the head of the humerus from the shaft of the humerus. The addition of the light-sensitive liquid 165 to the expandable member 170 causes the expandable member to expand. As the expandable member 170 is expanded by the entering light-sensitive liquid 165, the fracture of the humeral neck is reduced. Once orientation of the bone fragments is confirmed to be in a desired position, the light-sensitive liquid 165 can be cured to form the photodynamic implant 510, which can then be separated from the delivery catheter. In an embodiment, the photodynamic implant 510 is used to treat a three-part fracture or a four-part fracture of a humeral head. In an embodiment, the photodynamic implant 510 acts as a filler, mandrel or support element for fragments of the humeral head. In an embodiment, the photodynamic implant 510 fills the space within the humeral head to substantially return the hemural head to its anatomical shape. In an embodiment, fractured bone fragments can be placed over the photodynamic implant 510 to return the fragments to their respective substantially original, anatomical positions. In an embodiment, broken fragments can be secured in their respective substantially, original position by attaching the broken fragments to the photodynamic implant by bone fixation implants, such as bone screws, nails, pins and rods, among others. In an embodiment, the photodynamic implant 510 extends into the shaft of the humerus or is attached to another implant that extends into the shaft of the humerus to provide additional stability to the bone for the duration of the healing process.

In an embodiment, a bone implant system 100 of the present disclosure is used to treat a proximal femoral fracture, such as a femoral neck fracture. In an embodiment, a bone implant system 100 of the present disclosure is used to treat or stabilize a weakened femoral head.

Figure 7:
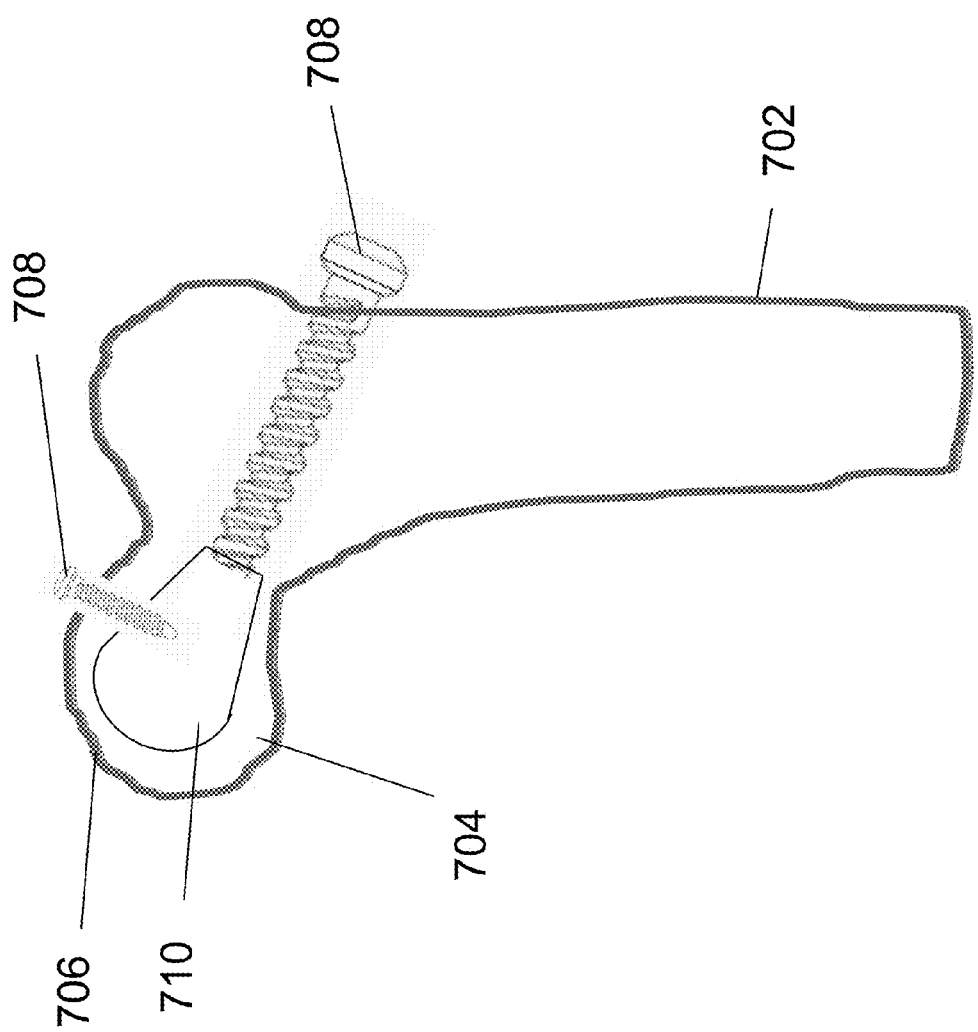
FIG. 7 shows a cross-sectional view of an embodiment of a device for treating a fractured or weakened head of a femur using the disclosed methods.

As shown in FIG. 7, in an embodiment, the photodynamic implant 710 is created inside an intramedullary space 704 within a head 706 of the femur 702, as described above. The broken fragments of the femur 702 can then be aligned and compressed together by placing a metal screw 708 or another bone fixation implant through the bone fragments or the side of the femur 702 into the photodynamic implant 710 in the femoral head 706. The force of compression on the bone fragments can be controlled by controlling the distance to which the screw 708 is driven into the photodynamic implant 710. The combination of the photodynamic implant 710 and a secondary implant, i.e. the screw 708, provides strength and stability to the femur 702. Alternatively or additionally, the photodynamic implant 710 can be configured to fill interstitial space between the bone fixation implant 708 and cortical bone surface inside the intramedullary cavity 704 to distribute load more evenly across the bone surface. That is, the photodynamic implant 710 acts as a filler between the bone fixation implant 708 and the cortical bone surface so that load is not transferred between the bone fixation implant 708 and the cortical bone through focal contact points between the bone fixation implant 708 and the cortical bone, but is rather distributed throughout a conformal contact created by the photodynamic implant 710.

In an embodiment, the present device includes a series of small interlocking metallic or plastic tubes that are inserted into the cavity of the bone, such as the medullary canal. In an embodiment, the series of tubes are used instead of or in addition to the use of the catheter The tubes are made from any suitable material including, but not limited to, a metal or a plastic. The tubes are interlocked sequentially to adjacent tubes such that the addition of the each incremental tube lengthens the entire tube.

In an embodiment, the tubes are slid over a mandrel and then locked or engaged to an adjacent tube in an end to end fashion. The interlocking mechanism of the sequential tubes is flexible so that the tubes can accommodate curvatures and deflections within the cavity of the bone. Since the series of tubes are flexible, the series of tubes are able to transit the length of the cavity of the bone without being obstructed within the canal as would a rigid length of tubing. Also, because the tube is flexible, a larger diameter tube or series of tubes may be interlocked and used within the cavity of a bone. A rigid tube would need to have a smaller diameter to navigate the deflections and curvatures within a cavity of a bone. The interlocking tubes may be of different diameters such that the tubes can accommodate different diameters and tapers within the cavity of the bone.

In an embodiment, once the tubes are all interlocked, the photodynamic monomer and the expandable member are inserted into and through the tube, the expandable member is inflated, and the photodynamic monomer is cured within the confines of the tube. In an embodiment, the use of the series of tubes and the monomer disposed within the series of tubes provides a stronger photodynamic implant.

It should be noted that although the present disclosure has been described with respect to treating fractures of the humerus and femur, those skilled in the art will recognize that the presently disclosed embodiments and methods can be used to treat other bones in the body, including but not limited to, a fractured or weakened tibia, fibula, ulna, radius, metatarsals, metacarpals, phalanx, phalanges, ribs, spine, vertebrae, clavicle and other bones.

In an embodiment, a device for restructuring or stabilizing a fractured or weakened head of a bone includes a delivery catheter having an elongated shaft with a proximal end, a distal end, and a longitudinal axis therebetween, the delivery catheter having an inner void for passing at least one light sensitive liquid, and an inner lumen; an expandable member releasably engaging the distal end of the delivery catheter, the expandable member moving from a deflated state to an inflated state when the at least one light sensitive liquid is passed to the expandable member; wherein the expandable member is sufficiently designed to be at least partially placed into a space within a head of a bone, and a light conducting fiber sized to pass through the inner lumen of the delivery catheter and into the expandable member, wherein, when the light conducting fiber is in the expandable member, the light conducting fiber is able to disperse the light energy to initiate hardening of the at least one light sensitive liquid within the expandable member to form a photodynamic implant.

In an embodiment, a method for repairing or stabilizing a fractured or weakened head of a bone includes placing a expandable member removably attached to a distal end of a delivery catheter into at least partially into a space within a head of a bone, infusing a light sensitive liquid into the expandable member through an inner lumen of the delivery catheter, inserting a light conducting fiber into the expandable member through an inner void of the delivery catheter, and activating the light conducting fiber to cure the light sensitive liquid inside the expandable member, thereby forming a photodynamic implant inside the head of the bone which serves as a mandrel or form for repair and stabilization of the head of the bone.

In an embodiment, a kit for repairing or stabilizing a fractured or weakened head of a bone includes an light conducting fiber; a unit dose of at least one light sensitive liquid; and a delivery catheter having an elongated shaft with a proximal end, a distal end, and a longitudinal axis therebetween, wherein the delivery catheter has an inner void for passing the at least one light sensitive liquid into a expandable member releasably engaging the distal end of the delivery catheter, and an inner lumen for passing the light conducting fiber into the expandable member, wherein the expandable member is sufficiently designed to be at least partially placed into a space within a head of a bone. In an embodiment, the kit includes a plurality of expandable members of different sizes or shapes. In an embodiment, the kit includes a light source.

In an aspect, a device for restructuring or stabilizing a fractured or weakened head of a bone includes: a delivery catheter having an elongated shaft with a proximal end, a distal end, and a longitudinal axis therebetween, an inner void for passing at least one light sensitive liquid, and an inner lumen; an expandable member releasably engaging the distal end of the delivery catheter; and a light conducting fiber sized to pass through the inner lumen of the delivery catheter and into the expandable member. The expandable member is capable of moving from a deflated state to an inflated state when the at least one light sensitive liquid is passed to the expandable member. The expandable member is sufficiently designed to be at least partially placed into a space within a head of a bone. When the light conducting fiber is in the expandable member, the light conducting fiber is able to disperse the light energy to initiate hardening of the at least one light sensitive liquid within the expandable member to form a photodynamic implant In one aspect, a method for repairing or stabilizing a fractured or weakened head of a bone includes: placing an expandable member removably attached to a distal end of a delivery catheter at least partially into a space within a head of a bone; infusing a light sensitive liquid into the expandable member through an inner lumen of the delivery catheter; inserting a light conducting fiber into the expandable member through an inner void of the delivery catheter; and activating the light conducting fiber to cure the light sensitive liquid inside the expandable member to form a photodynamic implant inside the head of the bone. In an embodiment, the expandable member has a tapered elongated shape.

In one aspect, a kit for repairing or stabilizing a fractured or weakened head of a bone includes: a light conducting fiber; at least one light sensitive liquid; a delivery catheter having an elongated shaft with a proximal end, a distal end, and a longitudinal axis therebetween, an inner void, and an inner lumen; and an expandable member releasably engaging the distal end of the delivery catheter. The expandable member is sufficiently designed to be at least partially placed into a space within a head of a bone. The delivery catheter has an inner void for passing the at least one light sensitive liquid into the expandable member, and an inner lumen for passing the light conducting fiber into the expandable member. In an embodiment, the kits includes a plurality of expandable members of different sizes or shapes. In an embodiment, the kit includes a light source.

All patents, patent applications, and published references cited herein are hereby incorporated by reference in their entirety. It will be appreciated that several of the above-disclosed and other features and functions, or alternatives thereof, may be desirably combined into many other different systems or application. Various presently unforeseen or unanticipated alternatives, modifications, variations, or improvements therein may be subsequently made by those skilled in the art.

What is claimed is:

1. A device for restructuring or stabilizing a fractured or weakened head of a bone comprising:
    a delivery catheter having an elongated shaft with a proximal end, a distal end, and a longitudinal axis therebetween, an inner void for passing at least one light sensitive liquid, and an inner lumen;
    an expandable member formed from conformance polymeric material, the expandable member releasably engaging the distal end of the delivery catheter, the expandable member trial fits into a space within a head of a bone by alternatingly moving from a deflated state to an inflated state and back to the deflated state only by at least one light sensitive liquid, when the at least one light sensitive liquid is passed in and out of the expandable member,
    wherein the expandable member is designed to be at least partially placed into the space within the head of the bone, directly in contact with the head of the bone and to form fit to a surface contact area within the space of the head of the bone;
    a light conducting fiber sized to pass through the inner lumen of the delivery catheter and into the expandable member, wherein, when the light conducting fiber is in the expandable member, the light conducting fiber is able to disperse light energy to initiate hardening of the at least one light sensitive liquid within the expandable member to form a photodynamic implant,
    wherein an amount of the light sensitive liquid is hardened within the trial fitted expandable member, such that a size and a shape of the formed photodynamic implant has a size and a shape of the space inside the head of the bone, so the head of the bone is restructured to a substantially original size and an original shape around the formed photodynamic implant; and wherein the expandable member includes two or more receptacles for receiving and engaging an intramedullary nail or rod positioned in an intramedullary canal of the bone, the two or more receptacles being formed by a section of the expandable member inverted inward, the two or more receptacles having a shape of an inward cavity with at least one side wall and a bottom face connecting the at least one side wall, wherein an end and a length of the intramedullary nail or rod are shaped to complementary fit into the shape of the two or more receptacles, so the end and the length of the intramedullary nail or rod are in contact with the at least one side wall and the bottom face of the two or more receptacles.

2. The device of claim 1, wherein the expandable member is from a group consisting of one of a pear shape, a bulb shape, a dome shape, a rounded shape or an elongated shape.

3. The device of claim 1, wherein the expandable member has a tapered elongated shape.

4. The device of claim 1, wherein the expandable member has a retrograde shape or an antegrade shape.

5. The device of claim 1, wherein the expandable member has a proximal end and a distal end, and a diameter of the proximal end of the expandable member that is larger than a diameter of the distal end of the expandable member.

6. The device of claim 1, wherein the expandable member has a proximal end and a distal end, and a diameter of the distal end of the expandable member that is larger than a diameter of the proximal end of the expandable member.

7. The device of claim 1, wherein the expandable member is designed to be contained within the head of the bone and to minor a size and a shape of an area of the space of the head of the bone.

8. The device of claim 1, wherein the expandable member includes a head section and a shaft section, and the expandable member is designed such that the head section can be placed within the head of the bone and the shaft section can extend for a length into a shaft of the bone.

9. The device of claim 1, wherein the photodynamic implant engages with at least one bone fixation implant, wherein the at least one bone fixation implant is inserted through the bone to engage the photodynamic implant.

10. The device of claim 9, wherein the at least one bone fixation implant is a screw, a rod, a pin, a nail, or some combination thereof.

11. The device of claim 1, wherein the light conducting fiber includes a core and a cladding disposed on the core, and the cladding has at least one cut therein to expose the core and configured to alter a light exuded from the light conducting fiber.

12. The device of claim 1, wherein the intramedullary nail or rod is capable of engaging with a bone fixation implant in the intramedullary canal of the bone to provide stability.

13. The device of claim 1, wherein the bottom face of the one or more receptacle engages the end of the intramedullary nail or rod, so the shape of the one or more receptacle form fits to the end and the length of at least one intramedullary nail or rod.

14. A kit for repairing or stabilizing a fractured or weakened head of a bone comprising:
a light conducting fiber;
at least one light sensitive liquid;
a delivery catheter having an elongated shaft with a proximal end, a distal end, and a longitudinal axis therebetween, an inner void, and an inner lumen; and
an expandable member formed from conformance polymeric material, the expandable member releasably engaging the distal end of the delivery catheter, the expandable member trial fits into a space within a head of a bone by alternatingly moving from a deflated state to an inflated state and back to the deflated state only by at least one light sensitive liquid, when the at least one light sensitive liquid is passed in and out of the expandable member, wherein the expandable member is designed to be at least partially placed into the space within the head of the bone, directly in contact with the head of the bone and to form fit to a surface contact area within the space of the head of the bone, and wherein the delivery catheter has the inner void for passing the at least one light sensitive liquid into the expandable member, and the inner lumen for passing the light conducting fiber into the expandable member, wherein an amount of the light sensitive liquid is cured within the trial fitted expandable member, such that a size and a shape of the trial fitted expandable member has a size and a shape of the space inside the head of the bone, so the head of the bone is restructured to a substantially original size and an original shape around the cured trial fitted expandable member; and wherein the expandable member includes two or more receptacles for engaging at least one intramedullary nail or rod positioned in an intramedullary canal of the bone, the two or more receptacles being formed by a section of the expandable member inverted inward, the two or more receptacles having a shape of an inward cavity with at least one side wall and a bottom face connecting the at least one side wall, wherein an end and a length of the at least one intramedullary nail or rod are shaped to complementary fit into the shape of the two or more receptacles, so the end and the length of the intramedullary nail or rod are in contact with the at least one side wall and the bottom face of the two or more receptacles.

15. The kit of claim 14, further comprising a plurality of expandable members of different sizes or shapes.

16. The kit of claim 14, further comprising a light source.

17. A method for repairing or stabilizing a fractured or weakened head of a bone comprising:
placing an expandable member removably attached to a distal end of a delivery catheter at least partially into a space within a head of a bone, the expandable member directly contacting with the head of the bone to form fit to a surface contact area within the space of the head of the bone and being formed from conformance polymeric material;
trial fitting a size and a shape of the expandable member to a size and a shape of the space of the head of the bone by alternating expansion and deflation of the expandable member only by at least one light sensitive liquid, when the at least one light sensitive liquid is passed in and out of the expandable member;
inserting a light conducting fiber into the expandable member through an inner void of the delivery catheter;
activating the light conducting fiber to cure the light sensitive liquid inside the expandable member to form a photodynamic implant inside the head of the bone,
curing an amount of the light sensitive liquid inside the trial fitted expandable member, such that a size and a shape of the formed photodynamic implant has a size and a shape of the space inside the head of the bone, so the head of the bone is restructured to a substantially original size and a shape around the formed photodynamic implant, wherein the formed photodynamic implant includes two or more receptacles formed by a section of the expandable member inverted inward, the two or more receptacles having a shape of an inward cavity with at least one side wall and a bottom face connecting the at least one side wall, and engaging an end and a length of at least one intramedullary nail or rod into the two or more receptacles located at a proximal end of the formed photodynamic implant, wherein the end and the length of the at least one intramedullary nail or rod are shaped to complementary fit into the shape of the two or more receptacles, so the end and the length of the intramedullary nail or rod are in contact with the at least one side wall and the bottom face of the two or more receptacles when the at least one intramedullary nail or rod is positioned in an intramedullary canal of the bone.

18. The method of claim 17, wherein the expandable member has a tapered elongated shape.

19. The method of claim 17, further comprising disposing a head section of the expandable member within the head of the bone and extending a shaft section of the expandable member for a length into the shaft of the bone.

20. The method of claim 17, wherein the at least one intramedullary nail or rod is a metallic intramedullary nail or rod capable of attaching to another implant that extends into the intramedullary canal of the bone to provide stability to the bone.

21. The method of claim 20, wherein the at least one intramedullary nail or rod is a screw, a pin, or some combination thereof.

22. The method of claim 17, wherein the bone is a femur or a humerus.

23. A method for repairing or stabilizing a fractured or weakened bone comprising:

placing an expandable member removably attached to a distal end of a delivery catheter at least partially into a space within a bone, the expandable member directly contacting with a head of the bone to form fit to a surface contact area within the space of the bone and being formed from conformance polymeric material;

alternating expansion and deflation only by at least one light sensitive liquid to trial fit a size and a shape of the expandable member to a size and a shape of the space of the bone, when the at least one light sensitive liquid is passed in and out of the expandable member;

inserting a light conducting fiber into the trial fitted expandable member through an inner void of the delivery catheter;

activating the light conducting fiber to cure the light sensitive liquid inside the trial fitted expandable member inside the bone;

curing an amount of the light sensitive liquid inside the trial fitted expandable member, such that a size and a shape of the trial fitted expandable member has a size and a shape of the space inside the bone, wherein the cured trial fitted expandable member includes two or more receptacles formed by a section of the expandable member inverted inward, the two or more receptacles having a shape of an inward cavity with at least one side wall and a bottom face connecting the at least one side wall;

engaging an end and a length of at least one intramedullary nail or rod into the two or more receptacles located at a proximal end of the cured trial fitted expandable member, wherein the end and the length of the at least one intramedullary nail or rod are shaped to complementary fit into the shape of the two or more receptacles, so the end and the length of the intramedullary nail or rod are in contact with the at least one side wall and the bottom face of the two or more receptacles when the at least one intramedullary nail or rod is positioned in an intramedullary canal of the bone; and restructuring the bone to a substantially original size and a shape around the trial fitted expandable member.

* * * * *

UNITED STATES PATENT AND TRADEMARK OFFICE
CERTIFICATE OF CORRECTION

PATENT NO. : 9,775,661 B2  
APPLICATION NO. : 13/553247  
DATED : October 3, 2017  
INVENTOR(S) : Robert A. Rabiner et al.

Page 1 of 1

It is certified that error appears in the above-identified patent and that said Letters Patent is hereby corrected as shown below:

In the Claims

In Claim 7, Column 21 Line 34:  
Delete "minor"  
Insert --mirror--

Signed and Sealed this  
Twenty-first Day of November, 2017

Joseph Matal  
*Performing the Functions and Duties of the*  
*Under Secretary of Commerce for Intellectual Property and*  
*Director of the United States Patent and Trademark Office*